(12) United States Patent
Wirtz et al.

(10) Patent No.: US 9,554,951 B2
(45) Date of Patent: *Jan. 31, 2017

(54) ABSORBENT ARTICLES WITH IMPROVED CORE

(71) Applicant: The Procter & Gamble Company, Cincinnati, OH (US)

(72) Inventors: Birgit Wirtz, Cologne (DE); Walter Pieter Hendrik Laurentius Van Der Klugt, Mechernich Satzvey (DE); Rodrigo Rosati, Frankfurt (DE); Ernesto G. Bianchi, Oberursel (DE); Aniruddha Chatterjee, Kelkheim (DE); Carsten Heinrich Kreuzer, Hofheim (DE); Holger Beruda, Schwalbach am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 93 days.

This patent is subject to a terminal disclaimer.

(21) Appl. No.: 13/929,922

(22) Filed: Jun. 28, 2013

(65) Prior Publication Data

US 2014/0005623 A1 Jan. 2, 2014

(30) Foreign Application Priority Data

Jun. 28, 2012 (EP) .................................... 12174130

(51) Int. Cl.
*A61F 13/15* (2006.01)
*A61F 13/539* (2006.01)
(Continued)

(52) U.S. Cl.
CPC ........... *A61F 13/539* (2013.01); *A61F 13/534* (2013.01); *A61F 13/535* (2013.01); *A61F 13/5323* (2013.01)

(58) Field of Classification Search
CPC .. A61F 13/532; A61F 13/5323; A61F 13/534; A61F 13/535; A61F 2013/530481; A61F 2013/53051; A61F 2013/530547; A61F 2013/530567; A61F 2013/530868; A61F 2013/530875; A61F 2013/530883

See application file for complete search history.

(56) References Cited

U.S. PATENT DOCUMENTS

| 3,848,594 A | 11/1974 | Buell |
| 3,860,003 B2 | 1/1975 | Buell |

(Continued)

FOREIGN PATENT DOCUMENTS

| DE | 10204937 A1 | 8/2003 |
| EP | 0 149 880 A2 | 7/1985 |

(Continued)

OTHER PUBLICATIONS

PCT International Search Report, mailed Aug. 13, 2013 (11 pages).
EPO International Search Report, dated Dec. 9, 2012 (6 pages).

*Primary Examiner* — Bradley Philips
(74) *Attorney, Agent, or Firm* — Wednesday G. Shipp

(57) ABSTRACT

An absorbent article comprising a wearer-facing topsheet, a backsheet and an absorbent core disposed between the topsheet and the backsheet, characterized in that the absorbent core comprises: a first absorbent layer comprising a first substrate, a layer of first superabsorbent polymer particles deposited on the first substrate, and a fibrous layer of thermoplastic adhesive material covering the layer of first superabsorbent polymer particles; a second absorbent layer, the second absorbent layer comprising a second substrate and a mixed layer deposited on the second substrate, the mixed layer comprising a mixture of second superabsorbent particles and cellulosic fibers, the first absorbent layer and the second absorbent layer being combined together such that at least a portion of the fibrous layer of thermoplastic (Continued)

adhesive material of the first absorbent layer contacts at least a portion of the mixed layer of the second absorbent layer, and wherein the first absorbent layer is placed closer to the topsheet than the second layer.

18 Claims, 15 Drawing Sheets

(51) Int. Cl.
  *A61F 13/534* (2006.01)
  *A61F 13/532* (2006.01)
  *A61F 13/535* (2006.01)

(56) References Cited

U.S. PATENT DOCUMENTS

| | | | |
|---|---|---|---|
| 3,911,173 A | 10/1975 | Sprague | |
| 3,929,135 A | 12/1975 | Thompson | |
| 4,324,246 A | 4/1982 | Mullane et al. | |
| 4,340,703 A | 7/1982 | Freppel | |
| 4,342,314 A | 8/1982 | Radel et al. | |
| 4,463,045 A | 7/1984 | Ahr et al. | |
| 4,507,438 A | 3/1985 | Obayashi et al. | |
| 4,515,595 A | 5/1985 | Kievit et al. | |
| 4,573,986 A | 3/1986 | Minetola et al. | |
| 4,609,518 A | 9/1986 | Curro et al. | |
| 4,629,643 A | 12/1986 | Curro et al. | |
| 4,662,875 B1 | 5/1987 | Hirotsu et al. | |
| 4,681,793 A | 7/1987 | Linman et al. | |
| 4,695,278 A | 9/1987 | Lawson | |
| 4,699,622 A | 10/1987 | Toussant et al. | |
| 4,710,189 A | 12/1987 | Lash | |
| 4,731,066 A | 3/1988 | Korpman | |
| 4,785,996 A | 11/1988 | Ziecker et al. | |
| 4,798,601 A * | 1/1989 | Shirose et al. | 604/368 |
| 4,808,178 A | 2/1989 | Aziz et al. | |
| 4,842,666 B1 | 6/1989 | Werenicz | |
| 4,846,815 A | 7/1989 | Scripps | |
| 4,894,060 A | 1/1990 | Nestegard | |
| 4,909,803 A | 3/1990 | Aziz et al. | |
| 4,946,527 A | 8/1990 | Battrell | |
| 4,963,140 A | 10/1990 | Robertson et al. | |
| 5,006,394 A | 4/1991 | Baird | |
| 5,137,537 A | 8/1992 | Herron et al. | |
| 5,151,092 A | 9/1992 | Buell et al. | |
| 5,221,274 A | 6/1993 | Buell et al. | |
| 5,242,436 A | 9/1993 | Weil et al. | |
| 5,281,683 A | 1/1994 | Yano et al. | |
| 5,331,059 A | 7/1994 | Engelhardt et al. | |
| 5,486,167 A | 1/1996 | Dragoo et al. | |
| 5,499,978 A | 3/1996 | Buell et al. | |
| 5,507,736 A | 4/1996 | Clear et al. | |
| 5,532,323 A | 7/1996 | Yano et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,574,121 A | 11/1996 | Irie et al. | |
| 5,576,266 A | 11/1996 | Flosenzier et al. | |
| 5,580,411 A | 12/1996 | Nease et al. | |
| 5,591,152 A | 1/1997 | Buell et al. | |
| 5,593,399 A | 1/1997 | Tanzer et al. | |
| 5,607,760 A | 3/1997 | Roe | |
| 5,609,587 A | 3/1997 | Roe | |
| 5,643,588 A | 7/1997 | Roe et al. | |
| 5,714,156 A | 2/1998 | Schmidt et al. | |
| H1732 H | 6/1998 | Johnson | |
| 5,830,202 A | 11/1998 | Bogdanski et al. | |
| 5,833,678 A | 11/1998 | Ashton et al. | |
| 5,837,789 A | 11/1998 | Stockhausen et al. | |
| 5,849,816 A | 12/1998 | Suskind et al. | |
| 5,865,823 A | 2/1999 | Curro | |
| 5,866,242 A | 2/1999 | Tan | |
| 5,938,648 A | 8/1999 | Lavon et al. | |
| 5,968,025 A | 10/1999 | Roe et al. | |
| 6,004,306 A | 12/1999 | Robles et al. | |
| 6,121,509 A | 9/2000 | Ashraf et al. | |
| 6,143,821 A | 11/2000 | Houben | |
| 4,795,454 C1 | 6/2001 | Dragoo et al. | |
| 6,265,488 B1 | 7/2001 | Fujino et al. | |
| 6,329,565 B1 | 12/2001 | Dutkiewicz et al. | |
| 6,432,098 B1 | 8/2002 | Kline et al. | |
| 6,472,478 B1 | 10/2002 | Funk et al. | |
| 6,503,979 B1 | 1/2003 | Funk et al. | |
| 6,645,569 B2 | 11/2003 | Cramer et al. | |
| 6,657,015 B1 | 12/2003 | Riegel et al. | |
| 6,664,437 B2 | 12/2003 | Sawyer et al. | |
| 6,716,441 B1 | 4/2004 | Osborne et al. | |
| 6,790,798 B1 * | 9/2004 | Suzuki et al. | 442/374 |
| 6,863,933 B2 | 3/2005 | Cramer et al. | |
| 6,872,444 B2 | 3/2005 | McDonald et al. | |
| 6,946,585 B2 | 9/2005 | London | |
| 6,972,011 B2 | 12/2005 | Maeda et al. | |
| 6,979,564 B2 | 12/2005 | Glucksmann et al. | |
| 7,112,621 B2 | 9/2006 | Rohrbaugh et al. | |
| 7,250,481 B2 | 7/2007 | Jaworek et al. | |
| 7,311,968 B2 * | 12/2007 | Ehrnsperger et al. | 428/327 |
| 7,537,832 B2 | 5/2009 | Carlucci et al. | |
| 7,652,111 B2 | 1/2010 | Hermeling et al. | |
| 7,744,576 B2 | 6/2010 | Busam et al. | |
| 7,744,713 B2 | 6/2010 | Blessing et al. | |
| 7,750,203 B2 | 7/2010 | Becker et al. | |
| 7,772,420 B2 | 8/2010 | Hermeling et al. | |
| 7,786,341 B2 | 8/2010 | Schneider et al. | |
| 7,838,722 B2 | 11/2010 | Blessing et al. | |
| 7,850,672 B2 | 12/2010 | Guidotti et al. | |
| 7,923,597 B2 * | 4/2011 | Ponomarenko et al. | 604/367 |
| 7,938,813 B2 | 5/2011 | Wang et al. | |
| 8,017,827 B2 | 9/2011 | Hundorf et al. | |
| 8,124,229 B2 | 2/2012 | Stueven et al. | |
| 8,202,957 B2 | 6/2012 | Stueven et al. | |
| 8,206,533 B2 | 6/2012 | Hundorf et al. | |
| 8,236,715 B2 | 8/2012 | Schmidt et al. | |
| 8,287,999 B2 | 10/2012 | Schmidt et al. | |
| 8,389,658 B2 | 3/2013 | Stueven et al. | |
| 2002/0072471 A1 | 6/2002 | Ikeuchi et al. | |
| 2003/0105190 A1 | 6/2003 | Diehl et al. | |
| 2003/0148684 A1 | 8/2003 | Cramer et al. | |
| 2005/0008839 A1 | 1/2005 | Cramer et al. | |
| 2005/0101929 A1 * | 5/2005 | Waksmundzki et al. | 604/378 |
| 2005/0107759 A1 * | 5/2005 | Waksmundzki | A61F 13/15658 604/378 |
| 2005/0159720 A1 | 7/2005 | Gentilcore et al. | |
| 2005/0165208 A1 | 7/2005 | Popp et al. | |
| 2006/0184146 A1 | 8/2006 | Suzuki | |
| 2007/0093164 A1 | 4/2007 | Nakaoka | |
| 2007/0093767 A1 | 4/2007 | Carlucci et al. | |
| 2007/0118087 A1 | 5/2007 | Flohr et al. | |
| 2008/0312617 A1 | 12/2008 | Hundorf et al. | |
| 2008/0312622 A1 | 12/2008 | Hundorf et al. | |
| 2008/0312623 A1 * | 12/2008 | Hundorf et al. | 604/366 |
| 2009/0192035 A1 | 7/2009 | Stueven et al. | |
| 2009/0318884 A1 | 12/2009 | Meyer et al. | |
| 2010/0305536 A1 | 12/2010 | Fernkvist et al. | |
| 2010/0312208 A1 | 12/2010 | Bond et al. | |
| 2011/0250413 A1 | 10/2011 | Lu et al. | |
| 2011/0268932 A1 | 11/2011 | Catalan et al. | |
| 2011/0319848 A1 | 12/2011 | McKiernan et al. | |
| 2012/0316526 A1 | 12/2012 | Rosati et al. | |
| 2012/0316527 A1 * | 12/2012 | Rosati | A61F 13/535 604/366 |
| 2012/0316528 A1 | 12/2012 | Kreuzer et al. | |
| 2012/0316529 A1 | 12/2012 | Kreuzer et al. | |

FOREIGN PATENT DOCUMENTS

| | | |
|---|---|---|
| WO | WO 90-15830 A1 | 12/1990 |
| WO | WO 93-21237 A1 | 10/1993 |
| WO | WO 95-16746 A1 | 6/1995 |
| WO | WO 95-34329 A1 | 12/1995 |
| WO | WO 2009-155265 A2 | 12/2009 |

* cited by examiner

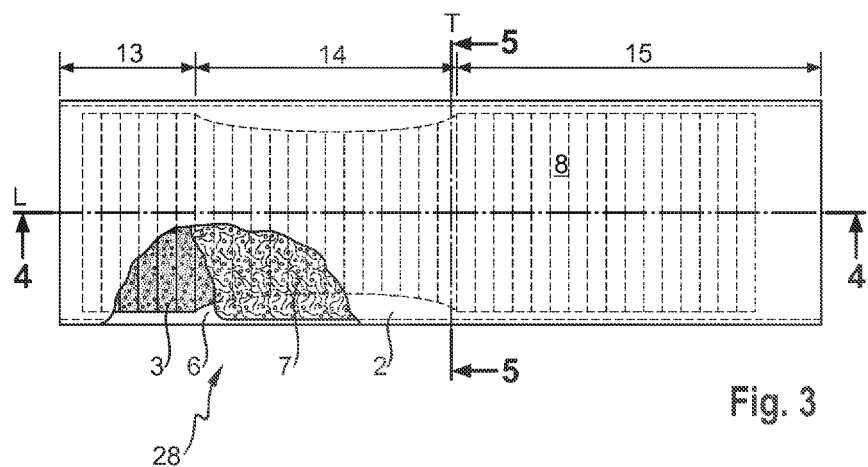

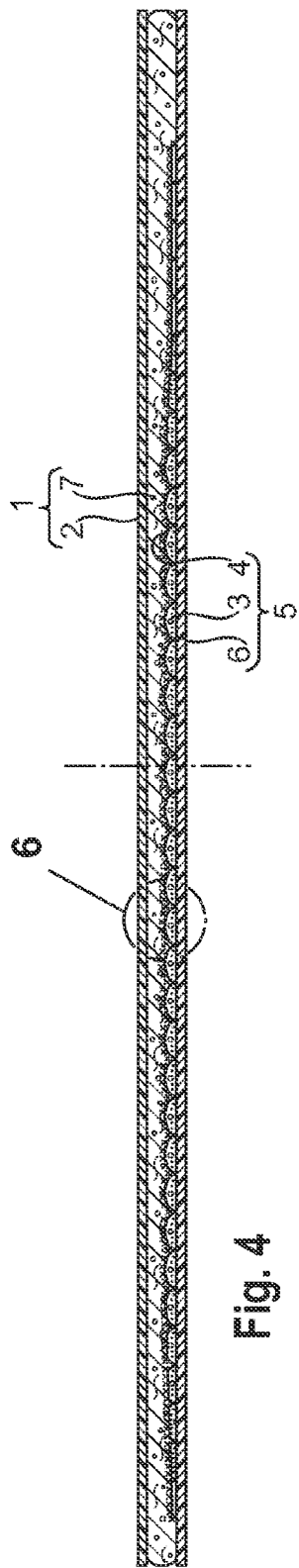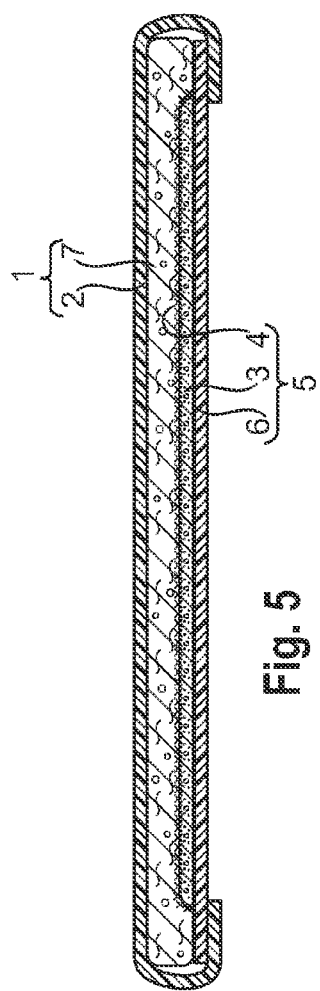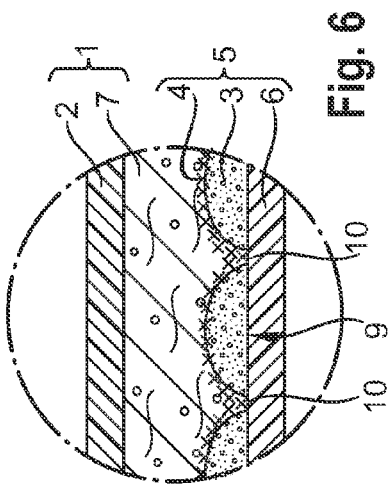

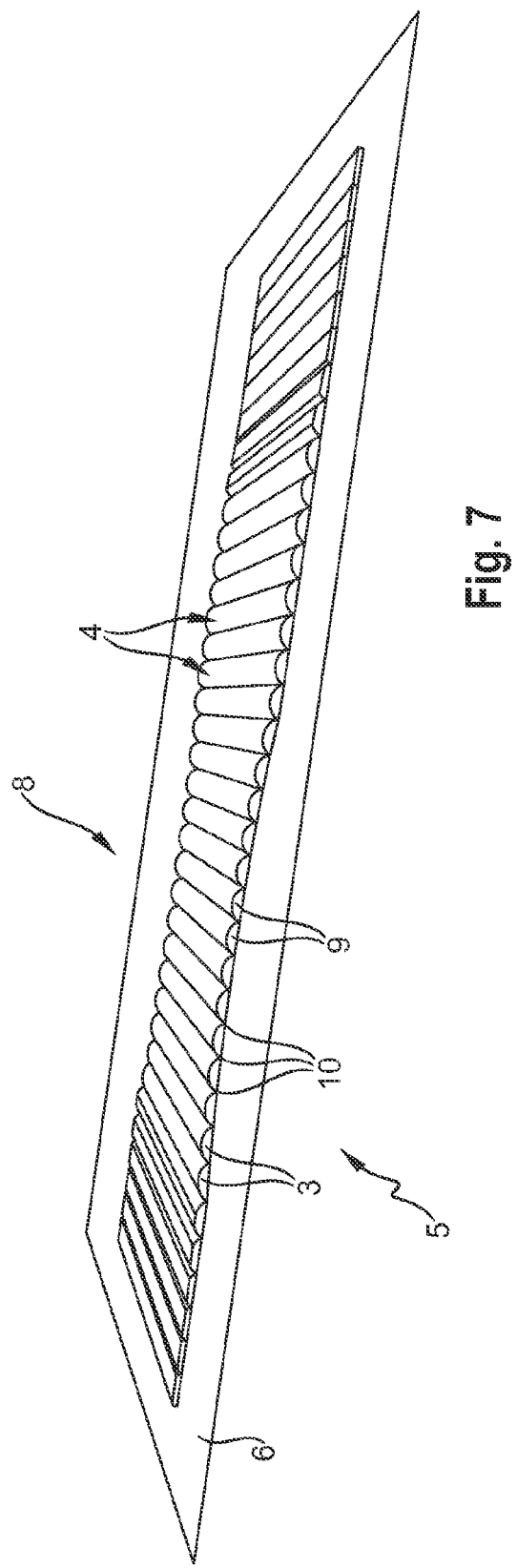

ABSORBENT ARTICLES WITH IMPROVED CORE

FIELD OF THE INVENTION

The present invention relates to absorbent articles such as diapers or feminine protection articles comprising an improved absorbent core.

BACKGROUND OF THE INVENTION

Absorbent articles for personal hygiene such as disposable infant diapers, feminine protection pads and adult incontinence undergarments, are designed to absorb and contain body exudates such as urine. These absorbent articles usually comprise several layers having different functions, for example a topsheet, a backsheet and in-between an absorbent core, among other layers. The absorbent core's function is to absorb and retain the exudates for a prolonged amount of time, for example overnight for a diaper, minimize re-wet to keep the wearer dry and avoid soiling of clothes or bed sheets.

The majority of currently marketed absorbent cores for diapers comprise as absorbent material a blend of comminuted wood pulp made of cellulose fibers ("Airfelt") with superabsorbent polymer particles (herein "SAP"), also called absorbent gelling materials (AGM). Typically the SAP are distributed in these cores so that they are more concentrated in the area where more fluid acquisition capacity is needed, in particular in the crotch (middle) region.

Absorbent cores can expand to several times their initial volumes when saturated and their performance can be impacted by the ability to maintain structural integrity, both in dry and wet conditions. At relatively high concentrations, the SAP tend to separate from the cellulose fibers and to move freely in the absorbent structure. It is thus desirable that the cores in the wet, expanded state, maintain their structural integrity and do not break or burst even when subjected to a shock such as a child sitting heavily on his diaper.

With this type of airfelt core, an increase of capacity to cover higher user loadings will also necessarily imply an increase of pulp or cellulose fiber amount and caliper, which impacts cost and fit. Furthermore, although it is desirable to increase the production speed of these absorbent cores, it becomes more and more difficult to accurately place the SAP according to the desired distribution as the production speed increases. The lack of precision of the distribution of SAP can be compensated by adding more of SAP, which is inefficient and expensive. It is desirable that absorbent cores should be thin (at least when dry) and require as little material as possible for cost and environmental reasons.

Over the last decades continued efforts have been made to develop new absorbent cores addressing these needs, as can be seen from the abundant patent literature. Absorbent articles having a core composed essentially of SAP as absorbent material (so-called "airfelt free" cores) have been proposed. For example US 2008/0312623 (Hundorf) describes an airfelt free core having absorbent particulate polymer material with a saline flow conductivity greater than about $100 \times 10^{-7}$ cm$^3$·sec/g such that even in the swollen state, i.e., when liquid has been absorbed, the liquid flow throughout the material is not substantially obstructed. However an increased permeability of the SAP is often gained at a cost of reduced absorbent capacity of such SAP. This may lead to increased usage of SAP in the absorbent structure to match the intended total product capacity. It can therefore be desirable to reduce or eliminate the utilization of such high permeable SAP. Additionally in general such airfelt free absorbent cores lack the flexibility for manufacturers to react to pulp/SAP price changes by accordingly adjusting the absorbent material formulation to match desired performance at the minimum cost.

U.S. Pat. No. 5,593,399 (Tanzer et al.) discloses disposable garments which include discrete pockets of superabsorbent polymer material held between a pair of carrier sheets to provide an absorbent laminate. The garment can comprise an absorbent structure which includes a retention portion having a primary absorbent portion, such as the absorbent laminate, for storing and holding absorbed liquids, such as urine. The retention portion can also include a supplemental absorbent, such as an outerside distribution layer, and alternatively or additionally include a bodyside distribution layer.

U.S. Pat. No. 5,830,202 (Bogdanski et al.) discloses an absorbent structure having a first layer comprising a mixture of AGM and cellulose and/or synthetic fibers, and a second layer comprising liquid-permeable substrate and AGM attached to the substrate thus forming a laminate. The laminate can be located on top of the mixed layer and defines an acquisition zone of low basis weight of AGM particles. The laminate may also be located below the mixed layer. The AGM may be attached to the substrate via a layer of adhesive applied to the substrate or the AGM may be coated by a stream of adhesive prior to contacting the substrate to form adhesively coated particles. Alternatively the AGM particles may be interconnected by the application of an interparticle cross-linking agent to form an interpartically cross-linked aggregate, in this case the AGM particles may be bonded to the substrate by the interparticle crosslinking agent. Finally it is also described the possibility to bond the AGM particles without the usage of an adhesive: the particles can be deposited onto a moist substrate such that the particles absorb moisture on their surfaces and become tacky; with subsequent drying of the moist substrate under application of pressure, resulting in attachment of the particles to the substrate. All of the methods above to attach and bond the AGM to the substrate have limitations, as they are limited to low AGM basis weight or are expensive or are effective only in dry or wet state but not in both conditions or have process issues particularly at high production speed.

Many other absorbent core designs have been proposed in the patent literature, for example U.S. Pat. No. 5,562,645 and 6,329,565 (both to Tanzer), U.S. Pat. No. 6,664,437 (Sawyer), U.S. Pat. No. 6,972,011B2 (Maeda), EP 1,447,066 (Busam), EP 631,768 (Plischke), US 2008/0312622 (Hundorf), U.S. Pat. No. 7,938,813 (Wang), U.S. Pat. No. 7,850,672 (Guidotti), WO 2009/008788 (Fernkvist), EP 1,632,206 (Nakaoka).

Although the currently practiced absorbent articles can provide very good fluid absorbency, fluid retention and fit, it is still desirable to find new and improved absorbent articles.

The present inventors have now developed absorbent articles comprising new absorbent cores, which can be produced at increased speed as well as providing design degrees of freedom in terms of profiling and shaping the distribution of SAP in the three spatial directions while keeping material costs as low possible. In particular the cores of the invention can deliver improved dry and wet immobilization of the superabsorbent particles, increase the overall integrity of the absorbent core structure compared to existing airfelt cores.

Furthermore the absorbent cores of the invention containing some amount of cellulose fibers allow increased design flexibility compared to airfelt-free core, can reduce or eliminate the utilization of high permeable SAP and provide flexibility for manufacturers to react to pulp/SAP price changes by accordingly adjusting the absorbent material formulation to match desired performance at the minimum cost.

SUMMARY OF THE INVENTION

The present invention relates to an absorbent article comprising a topsheet, a backsheet and an absorbent core disposed between the topsheet and the backsheet. The absorbent core used in the article of the invention comprises:
- a first absorbent layer comprising a first substrate and a mixed layer comprising a mixture of first superabsorbent polymer particles and cellulosic fibers deposited on the first substrate,
- a second absorbent layer comprising: a second substrate, a layer of second superabsorbent polymer particles deposited on the second substrate, and a fibrous layer of thermoplastic adhesive material covering the layer of second superabsorbent polymer particles.

The first absorbent layer and the second absorbent layer are combined together such that at least a portion of the fibrous layer of thermoplastic adhesive material of the second absorbent layer contacts at least a portion of the mixed layer of the first absorbent layer. The first absorbent layer is placed closer to the topsheet than the second layer.

BRIEF DESCRIPTION OF THE FIGURES

FIG. 3 is a top view of an exemplary absorbent core of the present invention with some layers partly removed;

FIG. 4 is a cross-section view of the absorbent core of FIG. 3 along its longitudinal axis L;

FIG. 5 is a cross-section view of the absorbent core of FIG. 3 along its transversal axis T;

FIG. 6 is a close-up view of part of the cross-section of FIG. 4;

FIGS. 7, 8 and 9 respectively show a perspective, top and cross-section view along the longitudinal axis of an embodiment of a second absorbent layer taken in isolation where the layer of second SAP is applied in a pattern of bars on the second substrate;

Definitions

The present invention relates to an absorbent article, in particular a personal hygiene absorbent article, comprising an improved absorbent core. As used herein, the term "absorbent article" refers to devices which are placed against or in proximity to the body of the wearer to absorb and contain the various exudates discharged from the body such as infant or adult diapers, feminine hygiene articles and the like. Typically these articles comprise a topsheet, backsheet, optionally an acquisition system (which may be comprised of one or several layers) and possibly other components, with the absorbent core normally disposed between the backsheet and the acquisition system or topsheet. The absorbent core is typically the component of the article having the most absorbent capacity. The term "absorbent core" as used herein does not include the topsheet, the backsheet and (if present) an acquisition system or layer which is not integral part of the absorbent core, in particular which is not placed between the first substrate and the second substrate.

A "nonwoven web" as used herein means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter ($g/m^2$ or gsm).

"Comprise," "comprising," and "comprises" are open ended terms, each specifies the presence of what follows, e.g., a component, but does not preclude the presence of other features, e.g., elements, steps, components known in the art, or disclosed herein. Elements introduced by terms such as "preferably", "typically", "in particular" are not essential unless otherwise indicated.

Overview

Figure 1:
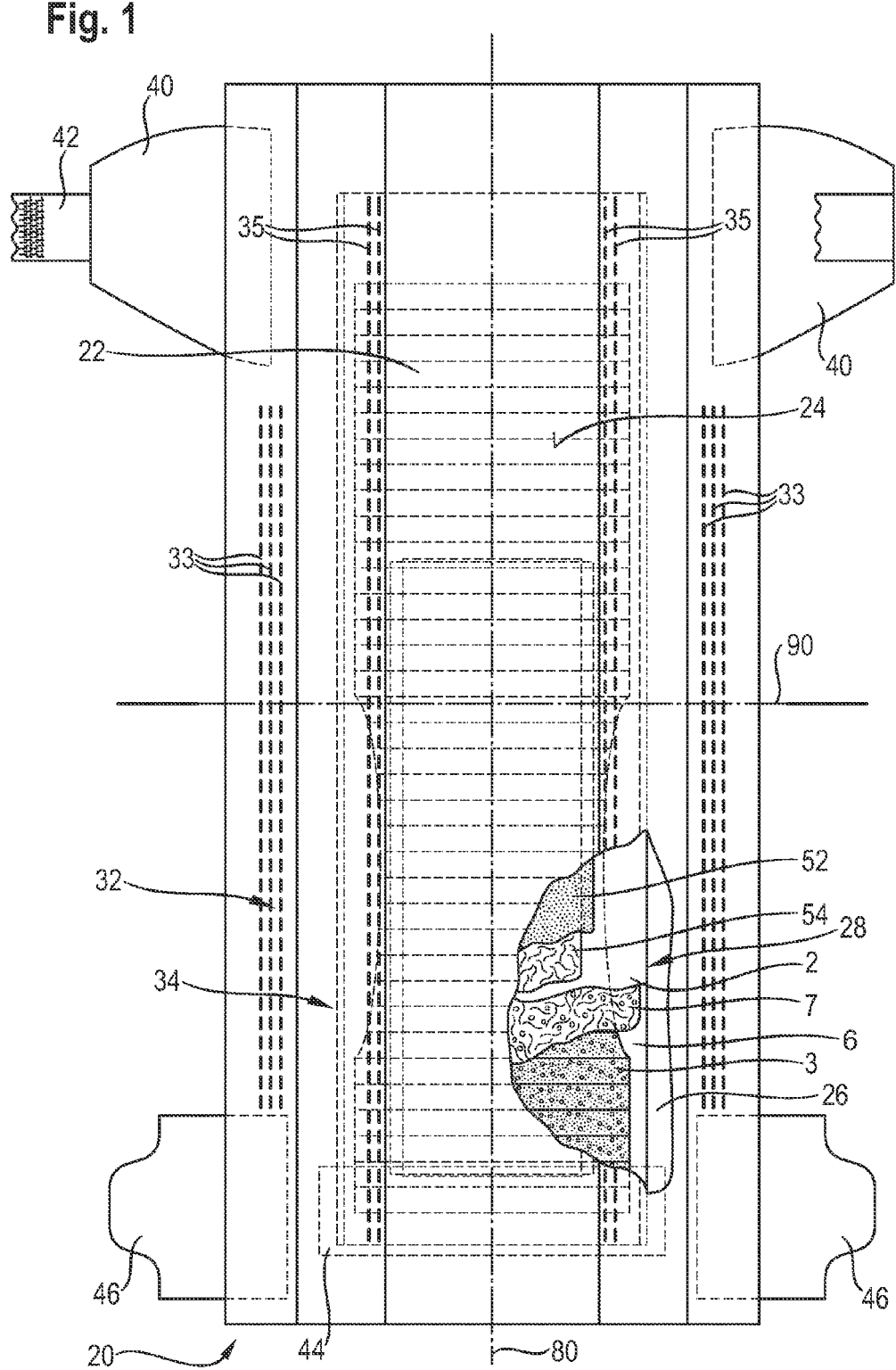
FIG. 1 is a top view of an absorbent article of the invention, exemplified as a diaper, with some layers partially removed.
Figure 2:
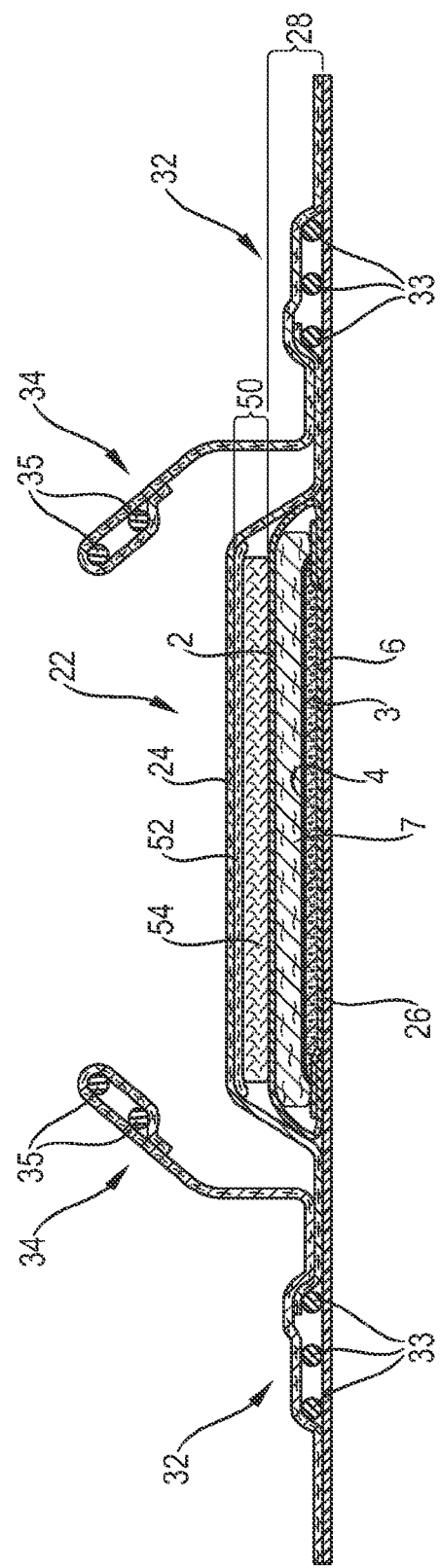
FIG. 2 is a cross-section view in the transverse direction of the absorbent article of FIG. 1.

An exemplary absorbent article in the form of an infant diaper 20 comprising an improved absorbent core of the invention is represented in FIGS. 1 and 2. In more details, FIG. 1 is a plan view of the exemplary diaper 20, in a flat-out state, with portions of the structure being cut-away to more clearly show the construction of the diaper 20. This diaper 20 is shown for illustration purpose only as the invention may be used for making a wide variety of diapers or other absorbent articles. In the following, the term "diaper" will be used for convenience, it being understood that what follows can be applied to any other type of absorbent articles unless specifically excluded.

The absorbent article, here represented as a diaper 20, comprises a liquid pervious topsheet 24, a liquid impervious backsheet 26, an absorbent core 28 disposed between at least a portion of the topsheet 24 and the backsheet 26, and can comprise other components such as an acquisition system or layer 50, elasticized leg cuffs 32 and barrier leg cuffs 34, and a fastening system which can comprise adhesive tabs 42 cooperating with a landing zone 44. The diaper may also comprise other elements, which are not represented, such as a back elastic waist feature, a front elastic waist feature, transverse barrier cuff(s), side panels or a lotion application.

The chassis 22 of the diaper 20 is the main body of the diaper and comprises the absorbent core 28 and an outer covering including the topsheet 24 and the backsheet 26 and the optional acquisition system or layer 50. The diaper 20 may be unitary, so that the chassis 22 comprises the main structure of the diaper with other features such as back ears 40 and/or barrier cuffs 34 attached to it to form the composite diaper structure. The topsheet 24, the backsheet 26, and the absorbent core 28 may be assembled in a variety of well known configurations, in particular by gluing or heat embossing. Exemplary diaper configurations are described generally in U.S. Pat. Nos. 3,860,003, 5,221,274 5,554,145, 5,569,234, 5,580,411, and U.S. Pat. No. 6,004,306.

The absorbent article 20 may be notionally divided by a longitudinal centerline 80 and a transverse centerline 90, dividing the article in approximately equal section in each direction.

The absorbent articles of the invention comprise an improved core 28 which is described in more details and individually with reference to FIG. 3 and the drawings that follow. The absorbent cores 28 of the invention comprise a first absorbent layer 1, which comprises a first substrate 2, a mixed layer 7 comprising a mixture of first superabsorbent particles and cellulosic fibers deposited on the first substrate, and a second absorbent layer 5 which comprises a second substrate 6, a layer 3 of second superabsorbent polymer particles deposited on the second substrate 6, and a fibrous layer of thermoplastic adhesive material 4 covering the layer 3 of second superabsorbent polymer particles.

The layer 3 of second SAP and the mixed layer 7 may be both deposited on their respective substrate in a rectangular pattern or one or both may be deposited in a non-rectangular (shaped) pattern, in particular a deposition area having a relatively narrow crotch section (e.g. as shown in FIG. 3 for the second absorbent layer). Channels in one or both absorbent layers may also be present (e.g. as shown in FIGS. 14 to 18).

As referred to herein, the longitudinal axis of the core L is the imaginary line separating the core 28 along its length in two substantially equal halves. The transversal axis T is the imagery line perpendicular to the longitudinal line of the core and going through the middle of the length of the core. The core may be symmetric relative to the longitudinal axis L. The core may be asymmetric along the transversal axis T, in order to adapt the core to the physiological need of the wearer, and in particular the core may have more absorbent capacity in its front half than its back half (the front half corresponding to the forward side of an absorbent article). In the Figures oriented as FIG. 3, the left side of the core represented is the side intended to be placed on the front of the absorbent article, although this is not limiting.

Some cores may be further conceptually divided along their length in three regions, the front 13, back 15 and middle 14 (or crotch) regions. The middle region is disposed between the front and back regions. In the middle region, the absorbent material of the first and/or second absorbent layers may in particular be distributed according to a relatively narrow width compared to the other two regions.

The cores of the invention may for example have a caliper at its thickest point (measured at a pressure of 0.3 psi) ranging typically from 1 to 10 mm, in particular from 1.5 to 5 mm, for example 2.5 mm. Of course the caliper may change along the surface of the absorbent core of the core is MD and/or CD profiled.

Some components of the core and the absorbent article will now be discussed in more detail.

First and Second Substrates 2, 6

The first and second substrates 2, 6 of the core may be formed of any materials suitable for receiving the absorbent materials to be deposited thereon. Typical substrate materials used in the production of conventional cores may be used, in particular paper, tissues, films, wovens or nonwovens, or laminate of any of these. The first and second substrates may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a SMS, SMMS, or SSMMS, structure, and having a basis weight range of about 5 gsm to 15 gsm. Other suitable materials are for example disclosed in US 2011/0268932A1, US 2011/0319848A1 or US 2011/0250413A1. Nonwoven materials provided from synthetic fibers may be used, such as PE, PET and in particular PP.

As the polymers used for nonwoven production are inherently hydrophobic, they are preferably provided with hydrophilic coatings if placed on the fluid receiving side of the absorbent core. A possible way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven. n alternative possible way to produce nonwovens with durably hydrophilic coatings is to coat the nonwoven with hydrophilic nanoparticles, e.g. as described in WO 02/064877.

The first substrate 2 and second substrate 6 may be made of the same material. The substrates may also be made of different materials or one of the substrate may be treated differently than the other to provide it with different properties. For example, the substrate intended to be closest to the wearer may be treated by a surface treatment to be more hydrophilic than the substrate on garment-facing side of the core.

Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A substrate having a lower contact angle between the water and the surface of substrate may be taken to be more hydrophilic than another.

Permanently hydrophilic nonwovens are also useful in some embodiments. Surface tension, as described in U.S. Pat. No. 7,744,576 (Busam et al.), can be used to measure how permanently a certain hydrophilicity level is achieved. Liquid strike through, as described in U.S. Pat. No. 7,744,576, can also be used to measure the hydrophilicity level. The first and/or second substrate may in particular have a surface tension of at least 55, preferably at least 60 and most preferably at least 65 mN/m or higher, and/or may also have a liquid strike through time of less than 5 s for a fifth gush of liquid, these values being measured using the test methods described in U.S. Pat. No. 7,744,576B2: "Determination Of Surface Tension" and "Determination of Strike Through" respectively.

The substrates may also be air-permeable. Films useful herein may therefore comprise micro-pores. The first and/or second substrate may have for example an air-permeability of from 40 or from 50, to 300 or to 200 $m^3/(m^2 \times min)$, as determined by EDANA method 140-1-99 (125 Pa, 38.3 $cm^2$). The first and/or second substrate may alternatively have a lower air-permeability, e.g. being non-air-permeable, for example to facilitate handling on a moving surface comprising vacuum.

As shown in FIGS. 1 and 3, the first substrate 2 may be placed on one side of the core (the top side as represented herein) and extends around the core's longitudinal edges to partially wrap the opposed (bottom) side of the core. The second substrate 6 can be positioned between the wrapped flaps of the first substrate 2 and the rest of the core. The flaps of the first substrate 2 and the second substrate 6 may be glued. This so called C-wrap construction can provide benefits such as improved resistance to bursting in a wet loaded state. As an alternate construction, in the so-called sandwich construction, the first and second substrates may extend outwardly and be sealed along the whole or parts of the periphery of the core, for example along the longitudinal edges of the core and/or the transversal edges, typically by gluing and/or heat/pressure bonding. The core may also be provided with end seals on both transversal edges.

First and Second Superabsorbent Polymer Particles (SAP)

The first absorbent layer 1 comprises first superabsorbent polymer particles ("first SAP") mixed with cellulosic fibers in the mixed layer and the second absorbent layer 5 comprises a layer 3 of second superabsorbent polymer particles ("second SAP") deposited on the second substrate 6. The first SAP and the second SAP can be provided from the same or different raw material, as will be detailed further below.

The SAP useful in the present invention include a variety of water-insoluble, but water-swellable polymers capable of absorbing large quantities of fluids. "Superabsorbent polymers" as used herein refer to absorbent material which are cross-linked polymeric materials that can absorb at least 10 times their weight of an aqueous 0.9% saline solution as measured using the Centrifuge Retention Capacity (CRC) test (EDANA method WSP 241.2-05E). The first and/or second superabsorbent polymer particles may in particular have a CRC value of more than 20 g/g, or more than 24 g/g, or of from 20 to 50 g/g, or from 20 to 40 g/g, or 24 to 30 g/g.

The superabsorbent polymer can be in particulate form so as to be flowable in the dry state. Typical particulate superabsorbent polymer materials are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. Suitable materials are described in the PCT Patent Application WO 07/047598 or for example WO 07/046052 or for example WO 2009/155265 and WO 2009/155264. In some embodiments, suitable superabsorbent polymer particles may be obtained by current state of the art production processes as are more particularly as described in WO 2006/083584. The superabsorbent polymers are preferably internally cross-linked, i.e. the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962 as well as crosslinkers described in WO 2009/155265. The superabsorbent polymer particles may be externally surface cross-linked, or: post cross-linked). Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, cyclic carbonates as described in DE-A 40 20 780, 2-oxazolidone and its derivatives, such as N-(2-hydroxyethyl)-2-oxazolidone as described in DE-A 198 07 502, bis- and poly-2-oxazolidones as described in DE-A 198 07 992, 2-oxotetrahydro-1,3-oxazine and its derivatives as described in DE-A 198 54 573, N-acyl-2-oxazolidones as described in DE-A 198 54 574, cyclic ureas as described in DE-A 102 04 937, bicyclic amide acetals as described in DE-A 103 34 584, oxetane and cyclic ureas as described in EP-A 1 199 327 and morpholine-2,3-dione and its derivatives as described in WO 03/031482.

In some embodiments, the superabsorbent polymer particles are formed from polyacrylic acid polymers/polyacrylate polymers, for example having a neutralization degree of from 60% to 90%, or about 75%, having for example sodium counter ions.

The superabsorbent polymer particles useful for the present invention may be of numerous shapes. The term "particles" refers to granules, fibers, flakes, spheres, powders, platelets and other shapes and forms known to persons skilled in the art of superabsorbent polymer particles. In some embodiments, the superabsorbent polymer particles can be in the shape of fibers, i.e. elongated, acicular superabsorbent polymer particles. In those embodiments, the superabsorbent polymer particles in the form of fibers have a minor dimension (i.e. diameter of the fiber) of less than about 1 mm, usually less than about 500 μm, and preferably less than 250 μm down to 50 μm. The length of the fibers is preferably about 3 mm to about 100 mm. The fibers can also be in the form of a long filament that can be woven.

Typically, superabsorbent polymer particles are spherical-like particles. In contrast to fibers, "spherical-like particles" have a longest and a smallest dimension with an aspect ratio of longest to smallest particle dimension in the range of 1-5, where a value of 1 would equate to a perfectly spherical particle and 5 would allow for some deviation from such a spherical particle. The superabsorbent polymer particles may have a particle size of less than 850 µm, or from 50 to 850 µm, preferably from 100 to 500 µm, more preferably from 150 to 300 µm, as measured according to EDANA method WSP 220.2-05. Superabsorbent polymer particles having a relatively low particle size help to increase the surface area of the absorbent material which is in contact with liquid exudates and therefore support fast absorption of liquid exudates.

The superabsorbent polymer particles may have a particle sizes in the range from 45 µm to 4000 µm, more specifically a particle size distribution within the range of from 45 µm to about 2000 µm, or from about 100 µm to about 1000 or to 850 µm. The particle size distribution of a material in particulate form can be determined as it is known in the art, for example by means of dry sieve analysis (EDANA 420.02 "Particle Size distribution).

In some embodiments herein, the superabsorbent material is in the form of particles with a mass median particle size up to 2 mm, or between 50 microns and 2 mm or to 1 mm, or preferably from 100 or 200 or 300 or 400 or 500 µm, or to 1000 or to 800 or to 700 µm; as can for example be measured by the method set out in for example EP-A-0 691 133. In some embodiments of the invention, the superabsorbent polymer material is in the form of particles whereof at least 80% by weight are particles of a size between 50 µm and 1200 µm and having a mass median particle size between any of the range combinations above. In addition, or in another embodiment of the invention, the particles are essentially spherical. Additionally or in yet another embodiment of the invention the superabsorbent polymer material has a relatively narrow range of particle sizes, e.g. with the majority (e.g. at least 80% or preferably at least 90% or even at least 95% by weight) of particles having a particle size between 50 µm and 1000 µm, preferably between 100 µm and 800 µm, and more preferably between 200 µm and 600 µm.

Suitable superabsorbent polymer particles may for example be obtained from inverse phase suspension polymerizations as described in U.S. Pat. Nos. 4,340,706 and 5,849,816 or from spray- or other gas-phase dispersion polymerizations as described in US Patent Applications No. 2009/0192035, 2009/0258994 and 2010/0068520. In some embodiments, suitable superabsorbent polymer particles may be obtained by current state of the art production processes as is more particularly described from page 12, line 23 to page 20, line 27 of WO 2006/083584.

The surface of the superabsorbent polymer particles may be coated, for example a cationic polymer. Preferred cationic polymers can include polyamine or polyimine materials. In some embodiments, the superabsorbent polymer particles may be coated with chitosan materials such as those disclosed in U.S. Pat. No. 7,537,832 B2. In some other embodiments, the superabsorbent polymer particles may comprise mixed-bed Ion-Exchange absorbent polymers such as those disclosed in WO-99/34841 and WO 99/34842.

As indicated previously, the first and second SAP may be the same or different materials. Using the same material simplifies the production of the cores as the same SAP storage unit maybe used as feed for both layers. On the other hand, having the opportunity to use two different SAPs gives more design freedom to create a desired flow rate in the storage core. For example a first SAP with relatively low UMP may be used in the first absorbent layer, because the cellulosic fibers mixed with the first SAP already increase the permeability of the first absorbent layer. The fluid permeability of a superabsorbent polymer can be quantified using its Urine Permeability Measurement (UPM) value, as measured in the test disclosed further below. Thus, it may be advantageous that the first SAP has a lower UPM than the second SAP, or the same can be used.

The UPM of the first SAP may be of at least $5 \times 10^{-7}$ cm$^3 \cdot$sec/g, at least $10 \times 10^{-7}$ cm$^3 \cdot$sec/g, at least $30 \times 10^{-7}$ cm$^3 \cdot$sec/g, or at least $50 \times 10^{-7}$ cm$^3 \cdot$sec/g. The UPM of the second SAP may for example be at least $30 \times 10^{-7}$ cm$^3 \cdot$sec/g, such as at least $50 \times 10^{-7}$ cm$^3 \cdot$sec/g, at least $70 \times 10^{-7}$ cm$^3 \cdot$sec/g, or at least $100 \times 10^{-7}$ cm$^3 \cdot$sec/g. Of course if the first and second SAP are made from the same material the UPM values will be the same, for example about $50 \times 10^{-7}$ cm$^3 \cdot$sec/g. The UPM of the SAP used is not particularly limited, as UPM of up to $2000 \times 10^{-7}$ cm$^3 \cdot$sec/g or more may be used.

The flow characteristics can also be adjusted by varying the quantity and distribution of the first and second SAP used in the first and second absorbent layer. The If the first and second SAP are different materials, the first SAP may have a higher CRC value than the second SAP.

The total weight ratio of the first SAP to the second SAP may for example range from 0.10 to 10, in particular from 0.2 to 5, from 0.3 to 3, or from 0.5 to 2, for example 1.

The weight ratio of the first SAP and cellulosic fibers contained in the mixed layer to the second SAP may for example range from 0.30 to 10, in particular from 0.5 to 3.

Second Superabsorbent Polymer Particle Deposition Area 8

The second superabsorbent polymer particles ("second SAP") are deposited on a deposition area 8 of the second substrate 6 to form a layer 3 of second SAP. The deposition area 8 of the second SAP on the second substrate 6 may typically be smaller than the available surface of the second substrate 6.

Figure 11:
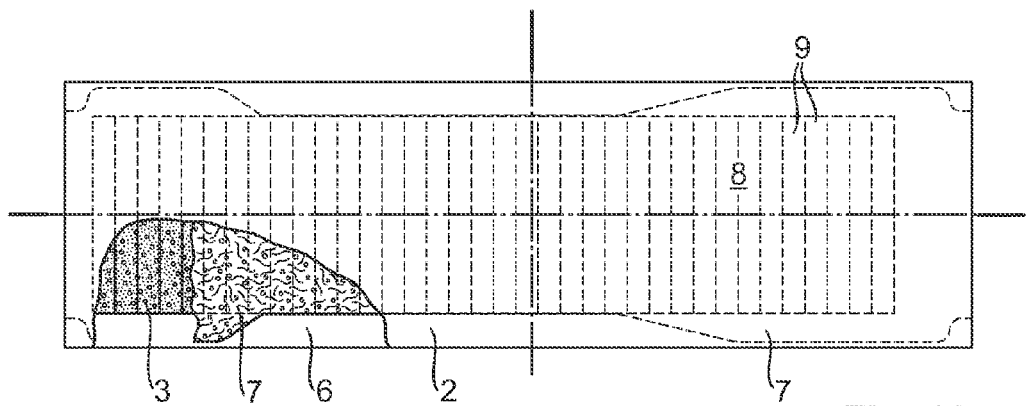
FIG. 11 shows an alternative absorbent core with the layer of second SAP applied as bars and having a rectangular deposition area and the mixed layer having a shaped non-rectangular (shaped) deposition area.
Figure 12:
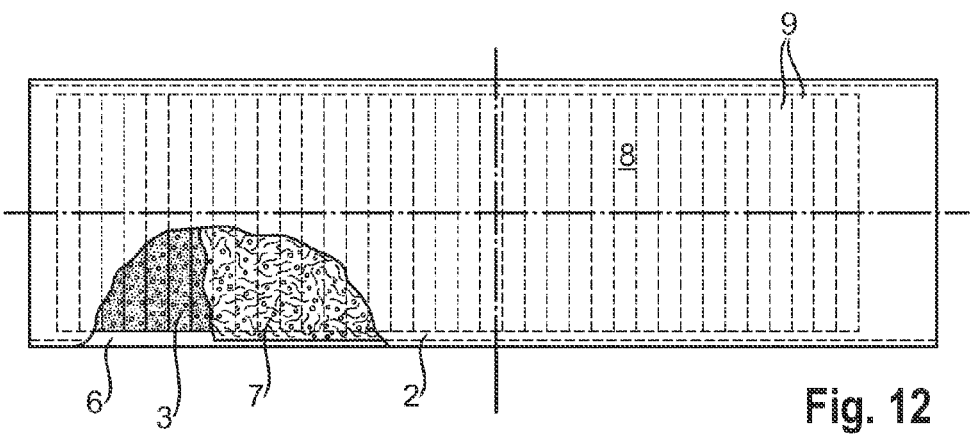
FIG. 12 shows an alternative absorbent core with the layer of second SAP and the mixed layer having both rectangular deposition areas.
Figure 14:
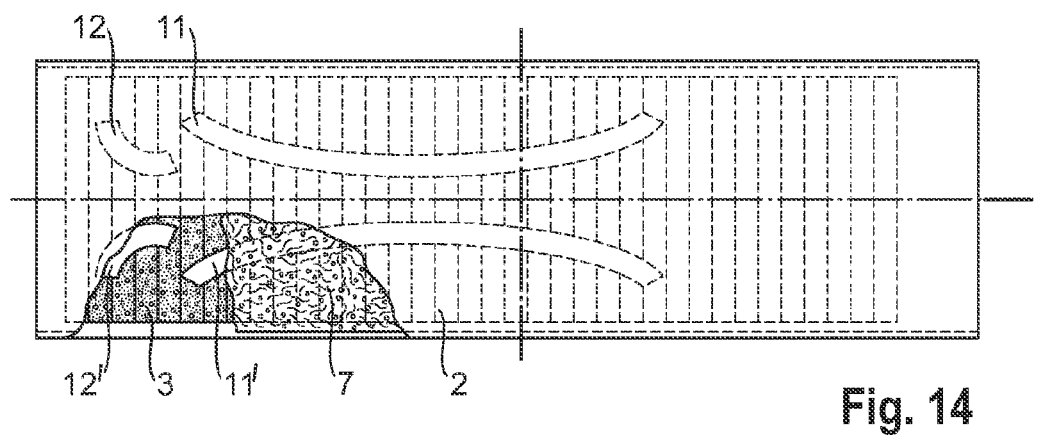
FIG. 14 shows a top view of an alternative absorbent core with channels in the second absorbent layer, the second absorbent layer having a rectangular deposition area.
Figure 15:
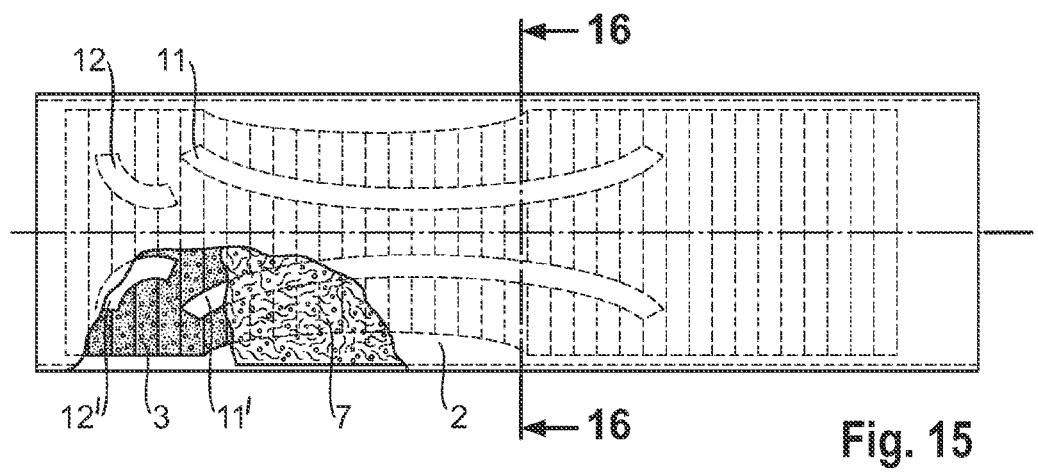
FIG. 15 shows a top view of an alternative absorbent core with channels in the second absorbent layer, the second absorbent layer having a shaped deposition area.

The deposition area 8 can take various shapes, in particular display a so-called "dog bone" or "hour-glass" shape, which shows a tapering along its width in the middle or "crotch" region of the core, as exemplarily shown in the embodiment of FIG. 3-7, or as a "T" or "Y" shape (e.g. as shown in FIG. 11). In this way, the second SAP deposition area may have a relatively narrow width in an area of the core intended to be placed in the crotch region of the absorbent article. This may provide for example better wearing comfort. The second SAP deposition area may thus have a width (as measured in the transversal direction) at its narrowest point which is less than about 100 mm, 90 mm, 80 mm, 70 mm, 60 mm or even less than about 50 mm. This narrowest width may further be for example at least 5 mm, or at least 10 mm, smaller than the width of the deposition area at its largest point in the front and/or back regions of the deposition area. The second SAP deposition area 8 can also be generally rectangular, for example as shown in FIG. 11, 12 or 14.

The deposition area 8 can be defined by its periphery. The layer 3 of second SAP may be uniformly deposited within the deposition area 8, but it will be typically advantageous to apply the second SAP discontinuously within the second SAP deposition area 8 in order to form land areas 9 comprising a relatively high amount of second SAP and junction areas 10 formed between the land areas with relatively low amount, and preferably substantially free of second SAP. In that case the second SAP deposition area 8 comprises the land areas 9 and the junction areas 10. Although the plural form is used, it is not excluded that the deposition area 8 comprises only a single connected land area and/or a single connected junction area, as seen for example in FIG. 10 having a single connected junction area 10. By "substantially free of SAP" it is meant that no SAP are intentionally deposited in the junction areas, but these may comprise isolated second superabsorbent particles involuntarily deposited due to process variability.

The land areas 9 thus can form discrete, or disconnected pockets of SAP enclosed on one side by the second substrate 6 and the other by the fibrous layer of adhesive material 4. The junction areas 10 can help the fibrous layer of thermoplastic adhesive material 4 to contact and adhere to the second substrate 6. This can provide a better immobilization of the layer of second SAP present in the land areas to the second substrate. In the land areas, the fibrous layer of thermoplastic adhesive material 4 typically does not contact the second substrate directly.

The land areas 9 and junction areas 10 can have a variety of shapes, including but not limited to, transversal and/or longitudinal bars, dots, circles, oval, square, rectangular, triangular, and the like. Within the second SAP deposition area 8, the total surface of the land areas 9 will typically be larger than the total surface of the junction areas 10.

The distance between two adjacent land areas as measured edge to edge (i.e. the minimum width of the junction areas between these land areas) may be relatively low, typically below 5 mm, 4 mm, 3 mm or less, and may be above 1 mm. This provides enough space for a good anchoring of the second SAP to the second absorbent layer in the junction areas while maintaining a large surface of land areas for absorbency. If not all, then at least a majority of the land areas may have such a distance. As the core is saturated with a fluid, the pockets of second SAP formed in the land areas will typically expand into the junction areas so that these will diminish up to a point where neighboring land areas will come into contact with each other. Typically, the junction areas will no longer be visible when the article is saturated with a fluid (e.g. after dipping in a Jayco Synthetic Urine solution as described further below).

In addition to the junction areas 10, the core may also comprise one or more, typically one or more pairs of, channels 11 which are typically much larger regions substantially free of second SAP, within the deposition area 8. The channels may typically extend substantially longitudinally and/or these channels will remain visible after saturation. These will be discussed further below.

Figure 8:
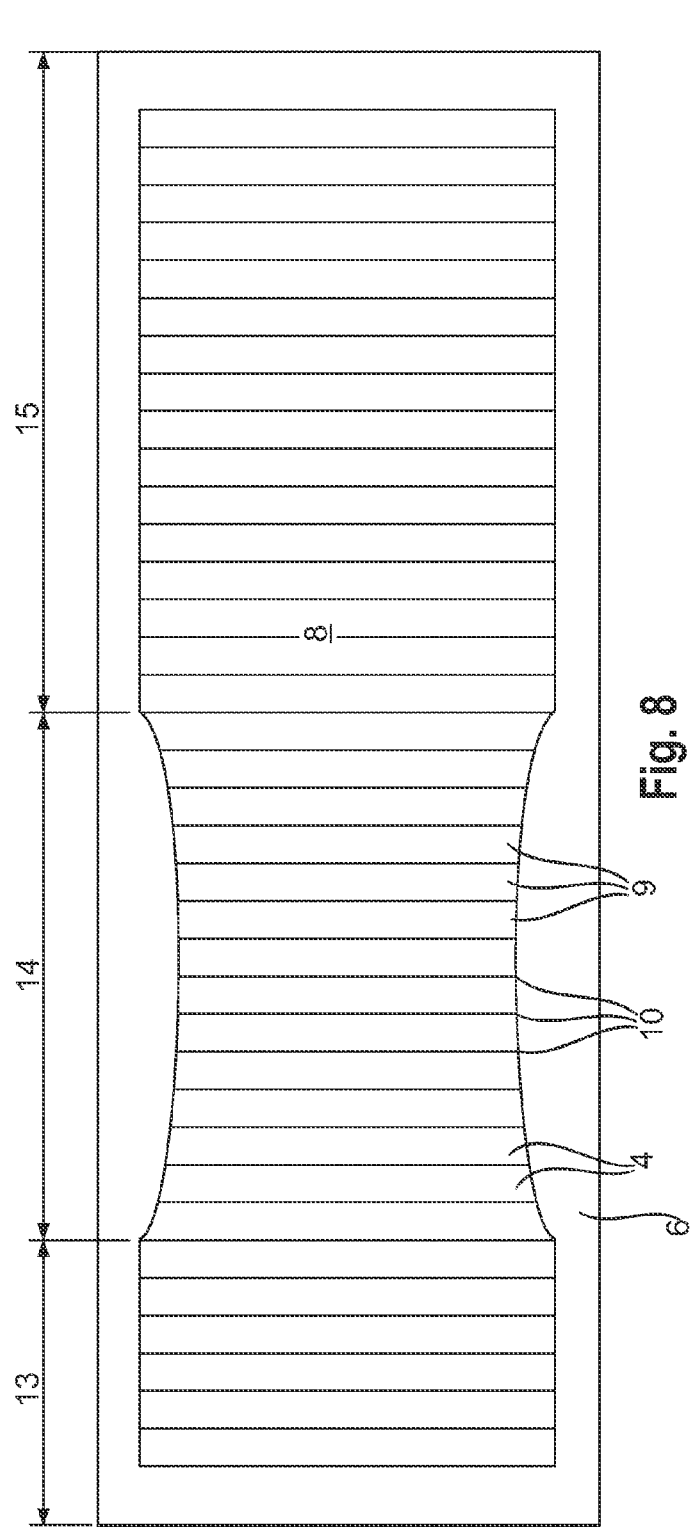
Figure 9:
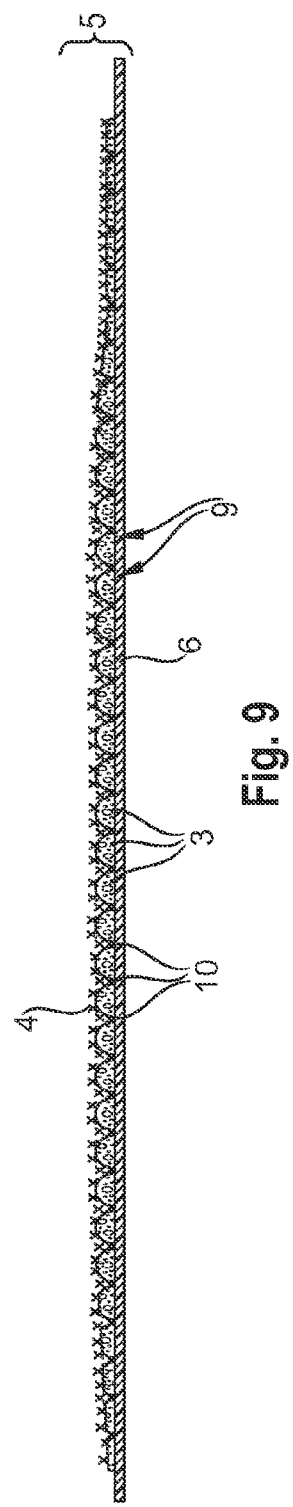

In the second SAP deposition area 8, the land areas 9 and the junction areas 10 may form transversally oriented alternating bars, as exemplarily shown in FIG. 3-6 and in more details in FIGS. 7-9 which show the second absorbent layer separately. The junction areas 9 are shown in particular in close up views of FIG. 6 and FIG. 9. In this embodiment, the land areas 9 may preferably be wider than the junction areas 10, as measured in the longitudinal direction. For example the land areas may have a width comprised between 2 and 40 mm, in particular between 4 and 20 mm, for example 10 mm, and the junction areas between these bars may have a width between 0.2 and 5 mm, or 0.5 and 4 mm, or 1 and 3 mm, for example 2 mm. The length of the bars may also vary in the transversal direction. For example it may be advantageous that the bars may be relatively shorter in the middle region 14 of the core and relatively longer at the front region 13 and/or the back region 15 of the core.

The basis weight (amount deposited per unit of surface) of the second SAP in the land areas 9 can be the same throughout the deposition area 8 or may be varied to form a profiled distribution of the second SAP in the longitudinal direction (e.g. as shown on FIG. 7), in the transversal direction, or both directions of the core. If the second SAP deposition area 8 is continuous so that there is not a plurality of land areas, then the basis weight within the deposition area may also be varied to form such a profiled distribution of SAP. The basis weight of SAP may be also be varied within a land area, for example to deposit more SAP in proximity to the longitudinal axis relative to the side of the core in a transversal bars execution.

Hence along the longitudinal axis of the core, the basis weight of the second SAP deposited in different land areas may be varied, as well as along the transversal axis, or any axis parallel to any of these axis. When the second SAP deposition pattern comprises land areas separated by junction areas, the basis weight of second SAP in a land area of relatively high basis weight may thus be for example at least 10%, or 20%, or 30%, or 40%, or 50% higher than in a land area of relatively low basis weight. In particular the land areas of the second SAP present in a deposition area having a narrowed width such as the middle region 14, or more generally a small surface area, may have on average more SAP per unit of surface deposited as compared to other deposition areas having a larger deposition area. The basis weight in these land areas may be inversely proportional to the width of these bars, as the process used to make the core may be arranged to deposit a regular amount of SAP by unit of length of second absorbent structure produced in the machine direction (in this case the longitudinal direction), but this is not limiting.

Figure 10:
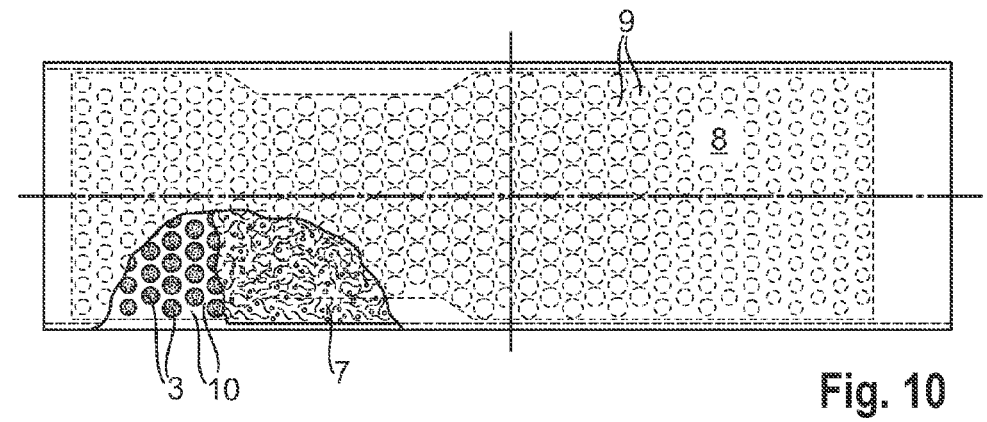
FIG. 10 is a top view of an alternative absorbent core with the second SAP applied as dots.

FIG. 10 shows another type of second SAP deposition area 8, wherein a grid pattern of substantially circular land areas is shown, each land area 9 being surrounded by a single connected junction area 10. In general, the land areas may be regularly spaced and sized, but the size and spacing of the land areas may also vary within the second SAP deposition area 8. Each circular land areas may also have different amount of SAP deposited per unit of surface. As shown in the example of FIG. 10 the size of the land areas (dots) may be larger in the central region of the core than in the front and back regions, and the basis weight of second SAP in each land area may also vary, e.g. with a higher basis weight in the middle region. The deposition area may comprise a narrower middle region, normally in the region of the core intended to be placed in the crotch area of the user in the finished article.

When the land areas are deposited in a grid pattern, for example of substantially circular land pattern as shown on FIG. 10, the surface of each land area may for example be comprised between 1 mm$^2$ and 100 mm$^2$, in particular 10 mm$^2$ and 50 mm$^2$, and the distance center to center between two adjacent land areas may be between 2 and 20 mm.

It is also possible to combine different patterns for the land areas, such as bars and dots (circular land areas), for example bars in the middle region of the core and dots on the front and the back. In fact, in one process of the invention, the second SAP are printed sequentially as a continuous series of dots which together form a bar when a relatively high amount of SAP is applied for each dot so that they overlap when printed. When a lower amount of second SAP is used for each dot, these dots may become smaller and distinct, so that a bar pattern and dot pattern can be combined on the same second SAP deposition area.

From the preceding, it is clear that with the cores of the invention, it is possible to design cores with a great freedom, in particular to best adapt the distribution of the second SAP in the area of the core where it will be most needed for the targeted user (e.g. according to the sex or the age of the baby) while keeping the core comfortable to wear.

It has been found that, for most absorbent articles such as diapers, the liquid discharge occurs predominately in the front half of the diaper. The front half of the absorbent core may therefore comprise most of the absorbent capacity of the core. Thus, the front half of the absorbent core may comprise more than about 60% of the second SAP, or more than about 65%, 70%, 75% or 80% of the second superabsorbent material.

The total amount of second SAP present in the absorbent core may also vary according to expected user. Feminine protection articles or diapers for new born may require much less SAP than infant or adult incontinence diapers. For infant diapers the total amount of second SAP may be for example comprised from about 1 to 50 g, in particular from 2 to 20 g. The average basis weight within the deposition area of the second SAP may be of at least 50, 100, 200, 300, 400, 500 or more g/m$^2$.

The second absorbent layer 5 may advantageously comprise little or no airfelt (cellulose) fibers mixed with the second SAP, in particular the second absorbent layer may be comprise less than 20%, 15%, 10%, 5% of airfelt fibers by weight of the second absorbent layer, or even be substantially cellulose free.

The layer of second SAP may be deposited using known techniques which allow relatively precise deposition of SAP at relatively high speed. In particular the SAP printing technology as disclosed for example in US 2006/24433 (Blessing), US 2008/0312617 and US 2010/0051166A1 (both to Hundorf et al.) may be used. This technique uses a printing roll to deposit SAP onto a substrate disposed on a grid of a support which may include a plurality of cross bars extending substantially parallel to and spaced from one another so as to form channels extending between the plurality of cross-bars. This technology allows high-speed and precise deposition of SAP on a substrate.

The second absorbent layer 6 may also comprise an auxiliary adhesive which is not illustrated in the figures. The auxiliary adhesive may be applied on the second substrate 6 before deposition of the layer 3 of second SAP for enhancing adhesion of the second SAP and the fibrous thermoplastic adhesive material 4 to second substrate 6. The auxiliary adhesive may comprise the same thermoplastic adhesive material that makes the fibrous layer covering the layer of second SAP but may also comprise other adhesives including but not limited to standard sprayable hot melt adhesives, such as H. B. Fuller Co. (St. Paul, Minn.) Product No. HL-1620-B, which may be cheaper than the thermoplastic adhesive material applied on the SAP of the second absorbent layer. The auxiliary adhesive may be applied to the second substrate by any suitable means, such as in about 0.5 to about 1 mm wide slots spaced about 0.5 to about 2 mm apart orientated in the Machine Direction of the core making process, typically longitudinal direction. The first or second absorbent layers may also optionally include a layer of construction glue to help the first and second absorbent layer adhering to each others, in particular the construction glue may be applied directly on the fibrous layer of thermoplastic adhesive material 4, as is illustrated in the exemplary process described below. U.S. Pat. No. 5,833,678 discloses examples of auxiliary adhesives and construction glues suitable for use in the present invention, as are also well known in the art.

Fibrous Layer of Thermoplastic Adhesive Material 4

The second absorbent layer 5 comprises a fibrous layer of thermoplastic adhesive material 4 which covers the layer 3 of second SAP. This layer (represented by crosses in the FIGS. 4-6, not shown in FIG. 3) is applied on the surface of the layer 3 formed by the deposited second SAP. The fibrous layer of thermoplastic adhesive material 4 may at least partially immobilize the second SAP in dry and wet state.

The term "fibrous layer" refers to a network of fibers of thermoplastic adhesive material which are applied in a molten state. The fibers are applied in a molten state directly to the surface of the layer formed by the second SAP where they form a fibrous layer by cooling. The second SAP directly in contact with the fibers are thus directly immobilized by the fibrous layer and the remaining SAP underneath are sandwiched between the second substrate and the fibrous layer.

The fibrous adhesive layer 4 may be at least partially in contact with the layer 3 of second SAP in the land areas 9 and at least partially in contact with the second substrate layer 6 in the junction areas 10 of the second absorbent layer. FIG. 6 shows in more detail such a structure, where the layer 3 of second SAP is provided as a discontinuous layer, and a layer 4 of fibrous thermoplastic adhesive material covers the layer 3 of second SAP, such that the thermoplastic adhesive material is in direct contact with the second SAP in land areas but also with the inner surface of the substrate in the junction areas. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the second SAP in the land area, and thereby immobilize this material.

Thus the fibrous layer of thermoplastic adhesive material can bond to the second substrate and at least partially affixes the second SAP to the second substrate. Thus, the fibrous thermoplastic adhesive material can immobilize the second SAP when wet, such that the absorbent core achieves an second SAP loss of no more than about 70%, 60%, 50%, 40%, 30%, 20%, or 10% according to the Wet Immobilization Test described in US 2010/0051166A1. Some thermoplastic adhesive material can also penetrate into both the second SAP and the second substrate, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive material may also provide a very good immobilization of absorbent material when the absorbent core is dry. The thermoplastic adhesive material may also be referred to as a hotmelt adhesive.

It has been found that those thermoplastic adhesive materials which are most useful for immobilizing the second SAP combine good cohesion and good adhesion behavior. Good adhesion may promote good contact between the thermoplastic adhesive material and the SAP and the substrate. Good cohesion reduces the likelihood that the adhesive breaks, in particular in response to external forces, and namely in response to strain. When the absorbent core absorbs liquid, the second SAP material swells and subjects the thermoplastic adhesive material to external forces. The thermoplastic adhesive material may allow for such swelling, without breaking and without imparting too many compressive forces, which would restrain the absorbent particulate polymer material from swelling.

The thermoplastic adhesive material may comprise, in its entirety, a single thermoplastic polymer or a blend of thermoplastic polymers, having a softening point, as determined by the ASTM Method D-36-95 "Ring and Ball", in the range between 50° C. and 300° C., and/or the thermoplastic adhesive material may be a hotmelt adhesive comprising at least one thermoplastic polymer in combination with other thermoplastic diluents such as tackifying resins, plasticizers and additives such as antioxidants.

The thermoplastic polymer may typically have a molecular weight (Mw) of more than 10,000 and a glass transition temperature (Tg) usually below room temperature or −6° C.<Tg<16° C. Typical concentrations of the polymer in a hotmelt are in the range of about 15 to about 50% by weight. The thermoplastic polymers may be water insensitive. Exemplary thermoplastic polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The tackifying resin may exemplarily have a Mw below 5,000 and a Tg usually above room temperature, typical concentrations of the resin in a hotmelt are in the range of about 30 to about 60%, and the plasticizer may have a low Mw of typically less than 1,000 and a Tg below room temperature, with a typical concentration of about 0 to about 15%.

The adhesive used for the fibrous layer preferably has elastomeric properties, such that the web formed by the fibers on the second SAP is able to be stretched as SAP swell. Exemplary elastomeric, hotmelt adhesives include thermoplastic elastomers such as ethylene vinyl acetates, polyurethanes, polyolefin blends of a hard component (generally a crystalline polyolefin such as polypropylene or polyethylene) and a soft component (such as ethylenepropylene rubber); copolyesters such as poly (ethylene terephthalate-co-ethylene azelate); and thermoplastic elastomeric block copolymers having thermoplastic end blocks and rubbery mid blocks designated as A-B-A block copolymers: mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprenestyrene block copolymer with polystyrene; and the elastomeric, hot-melt, pressure-sensitive adhesives described herein. Elastomeric, hot-melt adhesives of these types are described in more detail in U.S. Pat. No. 4,731,066 issued to Korpman on Mar. 15, 1988.

The thermoplastic adhesive material is applied as fibers. The fibers may have an average thickness of about 1 to about 50 micrometers or about 1 to about 35 micrometers and an average length of about 5 mm to about 50 mm or about 5 mm to about 30 mm. To improve the adhesion of the thermoplastic adhesive material to the second substrate or to any other layer, in particular any other nonwoven layer, such layers may be pre-treated with an auxiliary adhesive. The fibers adhere to each other to form a fibrous layer, which can also be described as a mesh.

In certain embodiments, the thermoplastic adhesive material will meet at least one, or several, or all of the following parameters. An exemplary thermoplastic adhesive material may have a storage modulus G' measured at 20° C. of at least 30,000 Pa and less than 300,000 Pa, or less than 200,000 Pa, or between 140,000 Pa and 200,000 Pa, or less than 100,000 Pa. In a further aspect, the storage modulus G' measured at 35° C. may be greater than 80,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. In a further aspect, the storage modulus G' measured at 90° C. may be less than 200,000 Pa and more than 10,000 Pa, or more than 20,000 Pa, or more then 30,000 Pa. The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high.

G' can be measured using a rheometer as indicated in of WO 2010/27719. The rheometer is capable of applying a shear stress to the adhesive and measuring the resulting strain (shear deformation) response at constant temperature. The adhesive is placed between a Peltier-element acting as lower, fixed plate and an upper plate with a radius R of e.g., 10 mm, which is connected to the drive shaft of a motor to generate the shear stress. The gap between both plates has a height H of e.g., 1500 micron. The Peltier-element enables temperature control of the material (+0.5° C.). The strain rate and frequency should be chosen such that all measurements are made in the linear viscoelastic region.

The thermoplastic adhesive material can be applied on the layer 3 of second SAP by a thermoplastic adhesive material applicator which may be a nozzle system which can spray a relatively thin but wide curtain of thermoplastic adhesive material. The thermoplastic adhesive material may preferably cover at least the whole of the deposition area of the fist SAP, but it is also possible to cover a portion of, or more than, the deposition area 8 of the layer of second SAP. The thermoplastic adhesive material may be applied uniformly at a basis weight of 1 gsm to 50 gsm, 5 to 20 gsm, e.g. 10 gsm of the area of the application of the thermoplastic adhesive material. The fibrous layer may also be applied at a basis weight which varies along the longitudinal axis, and/or the transversal axis or any other parallel axis (profiling).

First Absorbent Layer 1

The first absorbent layer 1 of the core comprises a first substrate 2 and a mixed layer 7 comprising a mix of first superabsorbent particles ("first SAP") and cellulosic fibers deposited on the first substrate. The first SAP and the cellulosic fibers may be homogenously mixed. The first absorbent layer 1 may also optionally includes an auxiliary adhesive between the first substrate 2 and the mixed layer 7 and/or a construction glue applied on the side of the mixed layer facing the second absorbent layer.

Figure 13:
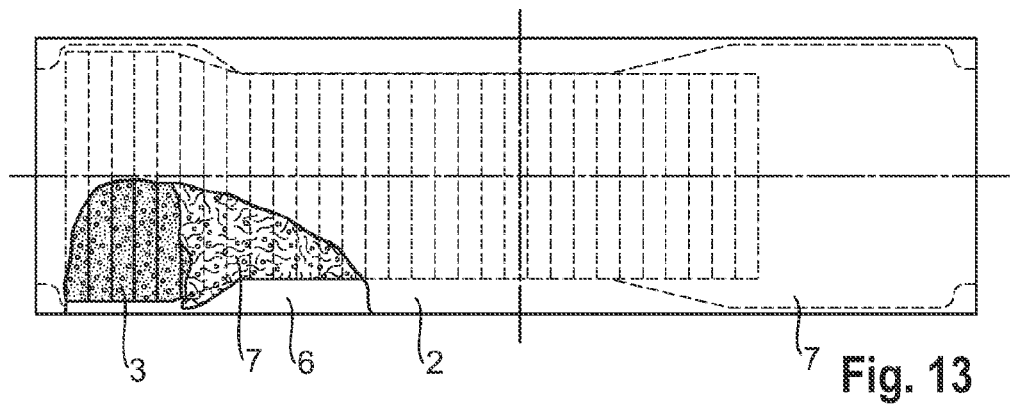
FIG. 13 shows an alternative absorbent core with the layer of second SAP and the mixed layer deposited in a non-rectangular area.

The deposition area of the mixed layer may have the same type of shape as indicated above for the deposition area of the layer of second SAP, in particular rectangular as exemplarily shown on FIGS. 3, 10, 12 and 14, or tapered with a narrower width in the middle or "crotch" region, in particular, "dog-bone", "sand-hour", "T" or "Y" shapes (see e.g. FIGS. 13 and 15) or others. The shapes of the deposition area of the layer of second SAP and the mixed layer can be combined as desired, usually taking into account the intended type of use of the core.

The mixed layer 7 comprises cellulosic fibers as is known in the art of core making, typically comminuted wood pulp which is generally referred to as airfelt and has some absorbency. Examples of other suitable absorbent materials which may be used in addition to the comminuted wood pulp include for instance creped cellulose wadding; meltblown polymers including coform; chemically stiffened, modified or cross-linked cellulosic fibers; synthetic fibers; etc. The mixed layer may comprise at least 25% of cellulose fibers by weight of the mixed layer, preferably a higher amount, such as at least 45%. The mixed layer may for example comprise from 25% to 80% by weight of the mixed layer of cellulose fibers and from 20% to 55% by weight of first SAP. The mixed layer may essentially or entirely consist of cellulose fibers and first SAP.

It is known in the art to make mixed absorbent layer of cellulosic fibers with SAP by mixing these in a mixing chamber and depositing the layer on a laying drum via vacuum. WO 2002/49565 (Sawyer) discloses for example a homogenous mixed layer and a method for making it. It is also known to form a profiled distribution of the SAP by pulsing the SAP in the forming chamber as relatively high speed so that the SAP is preferably distributed in the middle of the layer. The inventors have found that pulsing loses accuracy at relatively high speed of core making. The present invention can help obtaining a profiled distribution of AGM in the core via a relative precise distribution of AGM in the second layer while using a homogenous (non-profiled) mixed layer in the first absorbent layer. By homogenously mixed it is meant that there is no recognizable pattern of distribution of the first SAP in the first absorbent layer.

It may thus be advantageous that the mixed layer 7 is continuously distributed in its deposition area, preferably with a constant basis weight across its deposition area. The mixed layer may also be homogeneously mixed. Typical basis weight of the mixed layer ranges from 50 g/m$^2$ to 500 g/m$^2$, more particularly from 120 g/m$^2$ to 250 g/m$^2$, for example 200 g/m$^2$. The density of the mixed layer in the dry state (under 0.2 psi pressure) may for example range from 0.05 to 0.2 g/cc.

The weight ratio of the second SAP to the sum of the first SAP and cellulosic fibers contained in the mixed layer may for example range from 0.10 to 3.0, or 0.3 to 1.5, for example 0.5.

Combination of Both Absorbent Layers 1 and 5

The first and second absorbent layers are combined together such that at least a portion of the fibrous layer 4 of thermoplastic adhesive material of the second absorbent layer 5 contacts at least a portion of the mixed layer 7 of the first absorbent layer 1. The first and the second substrates form the external envelope of the resulting core.

A further adhesive ("construction glue", not represented in the Figures) may be used to improve the adhesion of the first absorbent layer with the second absorbent layer. The construction glue may be any standard hotmelt glue as known in the art. If present, the construction glue may be typically sprayed on the whole or part of the surface of the layer of the cross-linked cellulose fibers or the fibrous adhesive layer before combining the two absorbent layers. The construction glue may be applied for example to the whole or only part of the inner-facing surface of the first or second absorbent layer. Spraying construction glue for example will only create discrete points of bonding which do not substantially impact the passage of fluid between the absorbent layers or prevent at least partial contact between the layers.

If the deposition area of the fibrous thermoplastic adhesive material does not correspond to the whole of the surface of the second absorbent layer, for example if it is restricted to the whole or part of the deposition area 8 of the second SAP layer, then it may be advantageous to apply a construction glue at least in the areas of the first or second absorbent layer not contacting the fibrous thermoplastic adhesive material when both layers are combined, so to improve the adherence also in these areas, such as forming transversal end seals of the core.

In the absorbent article, the first absorbent layer with the mixed layer is orientated towards the wearer so that the first absorbent layer is the first one to be insulted by the fluid. Without wishing to be bound by theory, the mixed layer comprising a mix of first SAP and cellulosic fibers enables a fast acquisition of the gush insult thanks to the void volume, capacity and enhanced permeability provided by the airfelt matrix, even when first SAP having relatively low UPM values are used. The weight ratio of the airfelt and the first SAP can be further optimized to adjust the permeability and capacity of the mixed layer as desired. The second absorbent layer provides additional void volume upon swelling, flow rate and capacity to effectively prevent leakage.

Furthermore the second absorbent layer provides excellent dewatering of the first absorbent layer enabling the first absorbent layer to further dewater the upper layer such as the acquisition system/topsheet to provide excellent dryness benefits.

The cores of the invention can be produced with a profiled distribution of SAP at higher speed than conventional airfelt cores. The second SAP in the second absorbent layer can be sufficiently immobilized using the physical entrapment offered by the thermoplastic adhesive material. The complementing mixed layer does need to be profiled and thus this eliminates all challenges deriving from accelerating and decelerating ("pulsing") the first SAP and airfelt at high speeds as is known from conventional core making process. This results into a good SAP immobilization in the core whilst allowing also much higher line-speeds.

Channels 11, 12

The second SAP deposition area 8 may comprise, in addition to the relatively small junction areas 10 described before, relatively large zones which are substantially free of second SAP, and may take the form of channels 11, 12 contained within the second SAP deposition area 8, as exemplarily represented for example in FIG. 14 to 18. The mixed layer 7 deposition area may also comprise such channels.

These channels may be particularly advantageous to help the fluid to penetrate more quickly within the absorbent core. The second absorbent layer 5 may comprise one or more channels in the layer of second SAP, in particular one or more pairs of channels symmetrically arranged relative to the longitudinal axis L. Since the channels are substantially free of SAP, they will not swell when wet and will be typically clearly visible in wet state, whereas the junction areas which are much smaller and part of the deposition area may not be visible in wet state, as the second SAP will expand and may swell into the junction areas.

The channels 11 may in particular extend substantially longitudinally, which means typically that each channel extends more in the longitudinal direction than in the transverse direction, and typically at least twice as much in the longitudinal direction than in the transverse direction. The channels may also be present as one or several pairs 11, 11' in the absorbent layer, typically being symmetric about the longitudinal axis (i.e. taking the longitudinal axis as line of reflection). The first and second channels may be mirror images of one another with respect to the central longitudinal axis of the absorbent layer/core. In some embodiments, there may be no completely or substantially transverse channels present in at least the crotch region, or no such channels at all.

Thus, the channels 11 may be completely longitudinal and parallel to the longitudinal direction of the absorbent layer (i.e. parallel to the longitudinal axis); but also may be curved, provided the radius of curvature is typically at least equal (and preferably at least 1.5 or at least 2.0 times this average transverse dimension) to the average transverse dimension of the absorbent layer, and also straight but under an angle of (e.g. from 5°) up to 30°, or for example up to 20°, or up to 10° with a line parallel to the longitudinal axis. This may also includes channels with an angle therein, provided the angle between two parts of a channel is at least 120°, preferably at least 150°; and in any of these cases, provided the longitudinal extension of the channel is more than the transverse extension.

Each of the channels may have an average width W' that is least 4% of the average width W of the absorbent layer in which they are present, or at least 7% of W; and/or and up to 25% of W, or up to 15% of W. For a typical core to be used in a diaper. W' may be for example at least 5 mm; and for example up to 25 mm, or up to 15 mm.

Each of the first and second channels may have an average length L' (as measured in the longitudinal direction by projection on the longitudinal axis) which may for example be up to 80% of the average length L of the absorbent layer in which they are present; if the channels are only in the front region, or only in the crotch region, or only in the back region, L' is for example up to 25% of L, or up to 20% of L, and/or L' is for example at least 5% of L, or at least 10% of L. For a typical core to be used in a diaper, L' may be for example at least 10 mm, or at least 20 mm.

The channels are advantageously permanent channels, meaning their integrity is at least partially maintained when saturated with a fluid. Permanent channels may be obtained by provision of one or more adhesive material, for example the fibrous layer of adhesive material 4 or another adhesive that helps adhering for example a substrate within the walls of the channel. The Wet Channel Integrity Test described below can be used to test if channels are permanent following wet saturation and to what extent.

If both absorbent layers comprise channels which at least partially correspond to each other (overlap), permanent channels may be in particular formed by bonding the first substrate and the second substrate together through the channels. Typically, an adhesive can be used to bond both substrates through the channels, but it is possible to bond via other known means, for example ultrasonic bonding, or heat bonding. This adhesive may for example comprise one or more auxiliary adhesive which can be applied to any of the substrate, as indicated before, and/or the fibrous layer 4 of thermoplastic adhesive material. The substrates can be continuously bonded or intermittently bonded along the channels.

The channels may provide for fast liquid acquisition which reduces risk of leakages. The permanent channels help to avoid saturation of the absorbent layer in the region of fluid discharge (such saturation increases the risk of leakages). Furthermore, the inventors surprisingly found that, in contrast to what would be expected, whilst decreasing the overall amount of superabsorbent polymer material in the absorbent structure (by providing channels free of such material), the fluid handling properties of the absorbent structure, or diaper, are improved. Permanent channels, also have the further advantages that in wet state the absorbent material cannot move within the core and remains in its intended position, thus providing better fit and fluid absorption.

Advantageously, a permanent channel according to the invention has a percentage of integrity of at least 20%, or 30%, or 40%, or 50%, or 60, or 70%, or 80%, or 90% following the Wet Channel Integrity Test.

Figure 16:
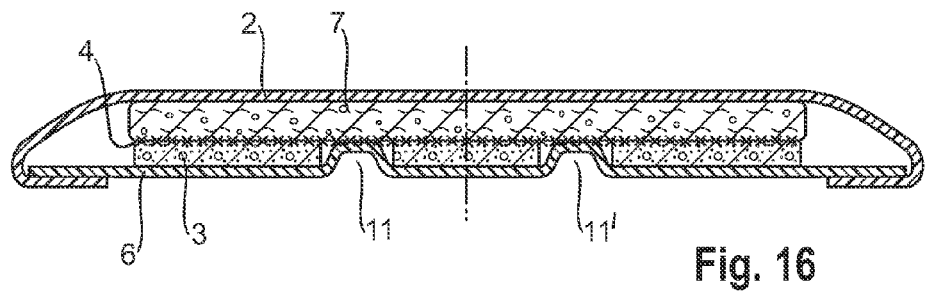
FIG. 16 shows a cross-section view of the core of FIG. 15.
Figure 18:
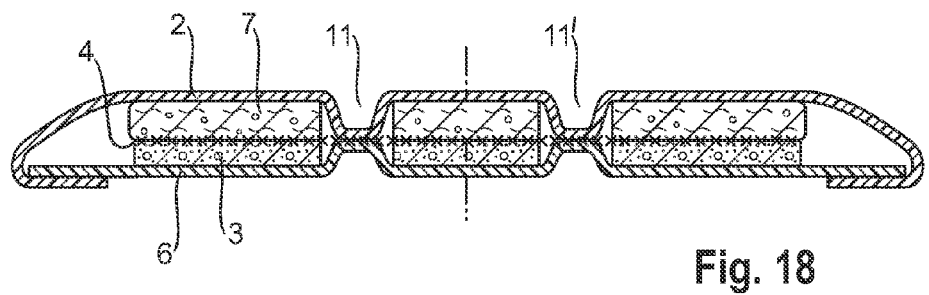
FIG. 18 shows a cross-section view of the core of FIG. 17.

As for the examples shown in FIGS. 16 and 18, one or more adhesive material(s) may be present between the first (or second) substrate and the corresponding absorbent material or parts thereof (e.g. herein referred to as, "second adhesive material"). For example, an adhesive material can be applied to portions of a substrate that are to coincide with the channels in the absorbent layer, so that in the channels the substrate can be bonded with the adhesive to the walls of the channel, or part thereof or to a further material. The adhesive may help immobilizing the absorbent material and avoid extensive migration thereof into the channels.

In some embodiments, and as for example shown in the Figures, there is no channel that coincides with the longitudinal axis L of the core. The channels in pair may be spaced apart from one another over their whole longitudinal dimension. The smallest spacing distance D may for example be at least 5% of average transverse dimension W of the corresponding absorbent layer, or for example at least 10% of W, or at least 15% of W; or for example at least 5 mm, or for example at least 8 mm.

Furthermore, in order to reduce the risk of fluid leakages, the longitudinal channels typically do not extend up to any of the transverse edges and/or longitudinal edges of the absorbent layer in which they are placed. Thus, the channels may be completely surrounded (in the horizontal plane) by the absorbent material of the absorbent layer in which they are present. Typically, the smallest distance I between a channel and the nearest longitudinal edge may correspond to at least 5% of W, or for example to at least 10% of W. In some embodiments, the distance is for example at least 10 mm; the smallest distance F between a channel and the nearest transverse edge of the absorbent layer may for example be at least 5% of the average length L of the absorbent layer.

Figure 17:
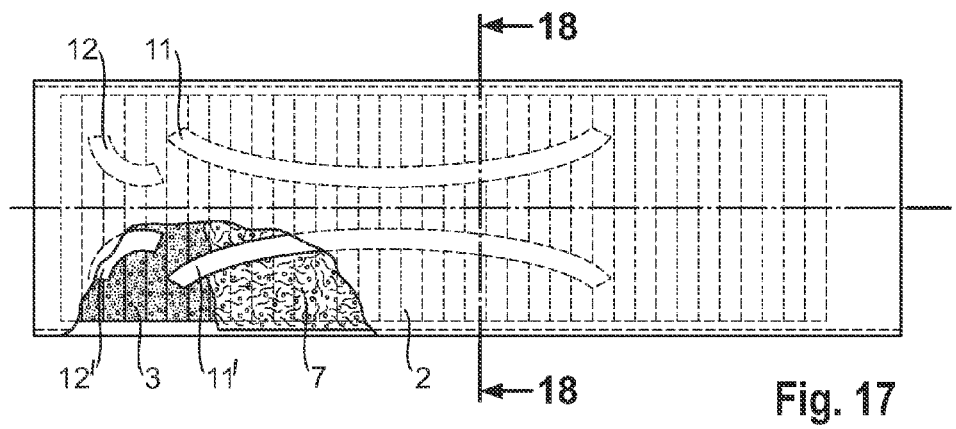
FIG. 17 shows a top view of an alternative absorbent core with channels in the first and second absorbent layers.

The absorbent core may comprise only two channels 11, 11', for example only in the front region, or for example in the central (crotch) region, and optionally extending into the front and/or back region, such as shown FIG. 17. The absorbent core may also comprise more than two of such channels, for example at least 4, or at least 5 or at least 6. Some or all of these may be substantially parallel to one another, for example being all straight and completely longitudinally, and/or two or more or all may be mirror images of one another in the longitudinal axis, or two or more may be curved or angled and for example mirror images of one another in the longitudinal axis, and two or more may be differently curved or straight, and for example mirror images of one another in the longitudinal axis. Shorter channels may also be present, for example in the front region of the core as represented in FIG. 14.

The channels in the second absorbent layer may be registered with channels in the first absorbent layer if these are present, as exemplarily shown on FIGS. 17 and 18. In that case the first and second substrate may be bonded through the channels via the fibrous adhesive layer 4 and/or an auxiliary glue and/or a construction glue if present.

In embodiments where the channels are present, the deposition area of the layer of second SAP may be non-rectangular (shaped), as shown in the Figures, but it is also explicitly considered that it may be rectangular, as channels may improve fit for the wearer so that the need for a shaped deposition area is less important. The mixed layer may in this case also be rectangular, or have another shape.

Backsheet 26

The backsheet 26 is generally that portion of the diaper 20 positioned adjacent the garment-facing surface of the absorbent core 28 and which prevents the exudates absorbed and contained therein from soiling articles such as bedsheets and undergarments. The backsheet 26 is typically impervious to liquids (e.g. urine). The backsheet may for example be or comprise a thin plastic film such as a thermoplastic film having a thickness of about 0.012 mm to about 0.051 mm. Exemplary backsheet films include those manufactured by Tredegar Corporation, based in Richmond, Va., and sold under the trade name CPC2 film. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some breathable composite materials are described in greater detail in WO 95/16746 published on Jun. 22, 1995 in the name of E. I. DuPont; U.S. Pat. No. 5,938,648 to LaVon et al., U.S. Pat. No. 4,681,793 to Linman et al., U.S. Pat. No. 5,865,823 to Curro; and U.S. Pat. No. 5,571,096 to Dobrin et al, U.S. Pat. No. 6,946,585B2 to London Brown.

The backsheet 26 may be joined to the topsheet 24, the absorbent core 28 or any other element of the diaper 20 by any attachment means known in the art (as used herein, the term "joined" encompasses configurations whereby an element is directly secured to another element by affixing the element directly to the other element, and configurations whereby an element is indirectly secured to another element by affixing the element to intermediate member(s) which in turn are affixed to the other element). For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173 4,785,996; and 4,842,666. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Topsheet 24

The topsheet 24 is the part of the absorbent article that is orientated towards and directly in contact with the wearer's skin when the article is worn. The topsheet can be attached to the backsheet, the core and/or any other layers as is known in the art. Suitable attachment means are described above with respect to means for joining the backsheet 26 to other elements of the diaper 20. Usually, the topsheet 24 and the backsheet 26 are joined directly to each other in some locations (e.g. on or close to the periphery of the diaper) and are indirectly joined together in other locations by directly joining them to one or more other elements of the diaper 20.

The topsheet 24 is preferably compliant, soft-feeling, and non-irritating to the wearer's skin. Further, at least a portion of the topsheet 24 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, meltblown, hydroentangled, or otherwise processed as is known in the art, in particular spunbond PP nonwoven. One suitable topsheet 24 comprising a web of staple-length polypropylene fibers is manufactured by Veratec, Inc., a Division of International Paper Company, of Walpole, Mass. under the designation P-8.

Suitable formed film topsheets are described in U.S. Pat. Nos. 3,929,135, 4,324,246, 4,342,314, 4,463,045, and 5,006,394. Other suitable topsheets 30 may be made in accordance with U.S. Pat. No. 4,609,518 and 4,629,643 issued to Curro et al. Such formed films are available from The Procter & Gamble Company of Cincinnati, Ohio as "DRI-WEAVE" and from Tredegar Corporation, based in Richmond, Va., as "CLIFF-T".

Any portion of the topsheet 24 may be coated with a lotion as is known in the art. Examples of suitable lotions include those described in U.S. Pat. Nos. 5,607,760, 5,609, 587, 5,635, 5,643,588, 5,968,025 and 6,716,441. The topsheet 24 may also include or be treated with antibacterial agents, some examples of which are disclosed in PCT Publication WO95/24173. Further, the topsheet 24, the backsheet 26 or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may be between about 10 cm$^2$ and about 50 cm$^2$, in particular between about 15 cm$^2$ and 35 cm$^2$. Examples of apertured topsheet are disclosed in U.S. Pat. No. 6,632,504, assigned to BBA NONWOVENS SIMP-SONVILLE. WO 2011/163582 also discloses suitable colored topsheet having a basis weight of from 12 to 18 gsm and comprising a plurality of bonded points. Each of the bonded points has a surface area of from 2 mm2 to 5 mm2 and the cumulated surface area of the plurality of bonded points is from 10 to 25% of the total surface area of the topsheet.

Typical diaper topsheets have a basis weight of from about 10 to about 21 gsm, in particular between from about 12 to about 18 gsm but other basis weights are possible.

Acquisition System 50

The diaper 20 may include one or more sublayer(s) disposed between the topsheet 24 and the backsheet 26 in addition to the absorbent core 28, as is known in the art. The sublayer may be any material or structure capable of accepting, storing or immobilizing bodily exudates. In particular the diapers may comprise an acquisition system 50 between the topsheet 24 and the absorbent core 28. The acquisition system 50 may be in direct contact with the first substrate 2 of absorbent core. The acquisition system 50 is desirable to quickly acquire the fluid and distribute across a larger area to maximize the use of the storage capacity of the core. The acquisition system 50 may function to receive a surge of liquid, such as a gush of urine. In other words, the acquisition system 50 may serve as a temporary reservoir for liquid until the absorbent core 28 can absorb the liquid.

The acquisition system 50 may comprise a single layer of an absorbent nonwoven or comprise multiple layers. The acquisition system may for example be a laminate of different nonwovens or an integral layer comprising different sub-layers for example airlaid layers integrated to form an unitary acquisition system as is known in the art. The acquisition system may comprise an upper acquisition layer 52 and a lower acquisition 54 layer. The acquisition system 50 may for example comprise as upper acquisition layer 52 comprising a nonwoven layer made of natural or synthetic fibers which may be treated by a surfactant to quickly acquire the fluid, and underneath a lower acquisition layer 54, which may comprise cross-linked cellulose fibers, to distribute the fluid across a larger surface, as will be discussed in more details below.

Upper Acquisition Layer 52

The upper acquisition layer 52 may typically be or comprise a non-woven material. Examples of suitable non-woven materials include, but are not limited to SMS or SMMS material, comprising a spunbonded, a melt-blown and a further spunbonded layer and alternatively a carded chemical-bonded nonwoven. The non-woven material may be latex bonded. Exemplary upper acquisition layers 52 are disclosed in U.S. Pat. No. 7,786,341. Carded, resin-bonded nonwovens may be used, in particular where the fibers used are solid round PET staple fibers (50/50 or 40/60 mix of 6 denier and 9 denier fibers). An exemplary binder is a butadiene/styrene latex.

The non-wovens may be porous. As polymers used for nonwoven production may be inherently hydrophobic, they may be coated with hydrophilic coatings. One way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven as described in US 2005/159720. Another way to produce nonwovens with durably hydrophilic coatings is to coat the nonwoven with hydrophilic nanoparticles, as described in U.S. Pat. No. 7,112,621 to Rohrbaugh et al. and in WO 02/064877.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co patent applications US 2003/148684 to Cramer et al. and US 2005/008839 to Cramer et al.

The upper acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). In certain embodiments, the binder may be present in the upper acquisition layer 52 in excess of about 12%, about 14% or about 16% by weight. SB latex is available under the trade name GENFLO™ 3160 (OMNOVA Solutions Inc.; Akron, Ohio).

Lower Acquisition Layer 54

The acquisition system 50 may comprise chemically cross-linked cellulosic fibers, in particular in a lower acquisition layer 54. Exemplary chemically cross-linked cellulosic fibers are disclosed in U.S. Pat. No. 5,137,537, WO 95/34329 and US 2007/118087. Polycarboxylic acids such as citric acid may be used as exemplary cross-linking agents. The chemically cross-linked cellulosic fibers may be cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Polyacrylic acids may also be used as cross-linking agents. The cross-linked cellulosic fibers may be crimped, twisted, or curled, or a combination thereof including crimped, twisted, and curled.

Examples of lower acquisition layer 54 may comprise about 70% by weight of chemically cross-linked cellulose fibers, about 10% by weight polyester (PET), and about 20% by weight untreated pulp fibers. In another example, the lower acquisition layer 54 may comprise about 70% by weight chemically cross-linked cellulose fibers, about 20% by weight lyocell fibers, and about 10% by weight PET fibers. In another example, the lower acquisition layer 54 may comprise about 68% by weight chemically cross-linked cellulose fibers, about 16% by weight untreated pulp fibers, and about 16% by weight PET fibers. In another example, the lower acquisition layer 54 may comprise from about 90-100% by weight chemically cross-linked cellulose fibers.

Fastening System 42, 44

The diaper 20 may also include a fastening system 42-44. The fastening system can be used to provide lateral tensions about the circumference of the diaper 20 to hold the diaper 20 on the wearer. The fastening system 42-44 usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the front waist region for the fastener to be releasably attached. Some exemplary surface fastening systems are disclosed in U.S. Pat. No. 3,848,594, 4,662,875, 4,846,815, 4,894,060 4,946,527 5,151,092 and 5,221,274 issued to Buell. An exemplary interlocking fastening system is disclosed in U.S. Pat. No. 6,432,098. The fastening system 42-44 may also provide a means for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. Nos. 5,242,436 5,499,978, 5,507,736, and 5,591,152.

Front and Back Ears 46, 40

The diaper 20 may comprise front ears 46 and back ears 40 as is known in the art. The ears can be integral part of the chassis, for example formed from the topsheet and/or backsheet as side panel. Alternatively, as represented on FIG. 1, they may be separate elements attached by gluing and/or heat embossing. The back ears 40 are advantageously stretchable to facilitate the attachment of the tabs 42 on the landing zone 40 and maintain the taped diapers in place around the wearer's waist. The back ears 40 may also be elastic or extensible to provide a more comfortable and contouring fit by initially conformably fitting the diaper 20 to the wearer and sustaining this fit throughout the time of wear well past when the diaper 20 has been loaded with exudates since the elasticized ears allow the sides of the diaper 20 to expand and contract.

Leg Cuffs 32

The diaper 20 may comprise leg cuffs 32 which provide improved containment of liquids and other body exudates. Leg cuffs 32 may also be referred to as leg bands, side flaps, barrier cuffs, or elastic cuffs. Usually each leg cuff will comprise one or more elastic string 33, represented in exaggerated form on FIG. 2 comprised in the chassis of the diaper for example between the topsheet and backsheet in the area of the leg openings to provide an effective seal while the diaper is in use. It is also usual for the leg cuffs to comprise "stand-up" elasticized flaps (barrier leg cuffs) 34 which improve the containment of the leg regions. Each barrier leg cuff typically comprises one or more elastic strings 35.

U.S. Pat. No. 3,860,003 describes a disposable diaper which provides a contractible leg opening having a side flap and one or more elastic members to provide an elasticized leg cuff (a gasketing cuff). U.S. Pat. No. 4,808,178 and U.S. Pat. No. 4,909,803 issued to Aziz et al. describe disposable diapers having "stand-up" elasticized flaps (barrier cuffs) which improve the containment of the leg regions. U.S. Pat. No. 4,695,278 and U.S. Pat. No. 4,795,454 issued to Lawson and to Dragoo respectively, describe disposable diapers having dual cuffs, including gasketing cuffs and barrier leg cuffs. In some embodiments, it may be desirable to treat all or a portion of the leg cuffs 32 with a lotion, as described above.

Elastic Waist Feature

The diaper 20 may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the end edge of the diaper 20. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

Method of Making the Absorbent Core and the Article

Figure 19:
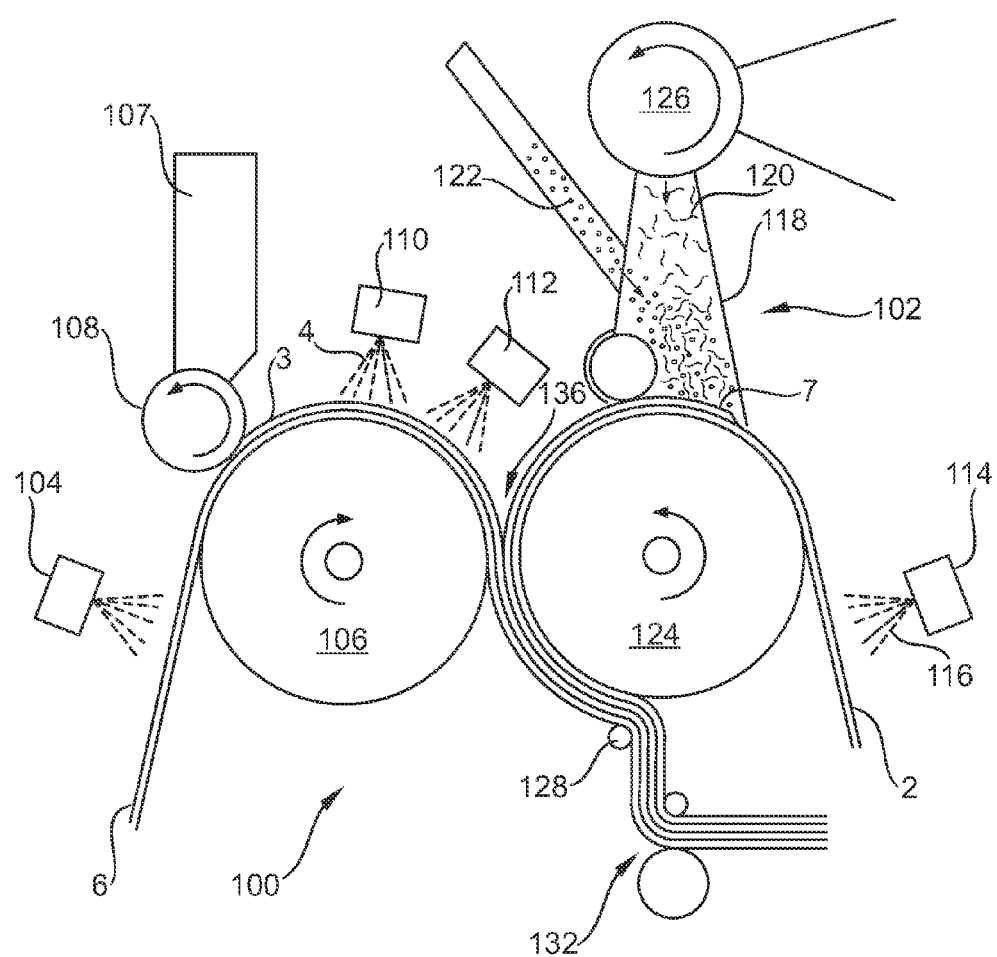
FIG. 19 is a schematic illustration of a process for making the cores of the invention.

The absorbent cores and articles of the invention may be made by any known suitable methods, including hand made for research purpose. A particularly suitable process for industrial production of the core combines a printing unit 100 for forming the second absorbent layer 5 and a mixing chamber and laying drum unit 102 for forming the first absorbent layer 1. Such an apparatus and method are exemplarily described on FIG. 19.

The printing unit 100 may be similar to one of the printing units described in US 2008/0312617A1. Such printing units may comprise an optional first auxiliary adhesive applicator 104 for applying an auxiliary adhesive to the second substrate 6, which may be a nonwoven web, a first rotatable support roll 106 for receiving the substrate 6, a hopper 107 for holding the second SAP, a printing roll 108 for transferring the second SAP to the substrate 6, and a thermoplastic adhesive material applicator 110 for applying the fibrous layer of thermoplastic adhesive material 4 to the layer 3 of second SAP. A construction glue applicator 112 may be optionally used to further apply a construction glue on the second absorbent layer 5, for example in area of the second substrate where the fibrous layer of thermoplastic adhesive material 4 was not applied.

The mixing chamber and laying drum unit 102 may comprise a second auxiliary adhesive applicator 114 for applying an optional auxiliary adhesive 116 to the first substrate 2, a mixing chamber 118 (deposition chute) for mixing and depositing a supply of pulp 120 and first SAP 122, a forming drum 124 for forming the mixed layer 7 on the first substrate 2. The supply of pulp material may be obtained by disintegrating an absorbent sheet in-feed using the disintegrator 126. As indicated previously, the first SAP may be pulsed through an injector 122 into the deposition chute 118 so that a gradient of SAP is created in the mixed layer. However it may be preferred, especially at high production speed, e.g. higher than 900 absorbent cores per minute, that the pulp and first SAP be mixed homogenously so that the first SAP are introduced continuously in the deposition chute.

The core making system 100-102 can also includes a guide roller 128 for guiding the formed absorbent core from a nip 130 between the first rotatable support rolls 140 and the laying drum and a further compression point formed by two calendaring rolls 132 for compressing the first and second absorbent layers to a desired density. Typically the cores of the invention may have a density of from 0.05 to 0.5 g/cm$^3$ after production, but other values are of course not excluded, for example further compression may happen when the core is integrated in an article or during packing of this article. A C-wrap folding unit and a cutting unit may also be present (not represented).

The first and second auxiliary adhesive applicators 112 and 114 may be any suitable available glue applicator. The fibrous layer of thermoplastic adhesive material applicator 110 may for example comprise a nozzle system which can provide a relatively thin but wide curtain of thermoplastic adhesive material.

Further details of the construction of the printing unit are exemplarily given in 2008/0312617A1, see in particular FIG. 11-14 of this application and the corresponding description section. In particular, the rotatable support roll 106 may comprise a rotatable drum and a peripheral vented support grid for receiving the second substrate 6. The printing roll 108 can comprise a rotatable drum and a plurality of absorbent particulate polymer material reservoirs in a peripheral surface of the drum. The reservoirs may have a variety of shapes, including cylindrical, conical, or any other shape. The reservoirs may lead to an air passage in the drum and comprise a vented cover for holding absorbent particulate polymer material in the reservoir and preventing the absorbent particulate polymer material from falling or being pulled into the air passage.

In operation, the first and second substrates 2 and 6 may be received into the mixing unit 102 and printing unit 100, respectively and further treated according to the following process. The second substrate 6 is drawn by the rotating support roll 106 past the first auxiliary adhesive applicator 104 which applies the second auxiliary adhesive to the second substrate 6 in a desired pattern. A vacuum (not shown) within the support roll 106 draws the second substrate 6 against the vertical support grid and holds the second substrate 6 against the first support roll 106. This presents an uneven surface on the substrate 2. Due to gravity, or by using the vacuum means, the substrate 2 will follow the contours of the uneven surface and thereby the substrate 2 will assume a mountain and valley shape. The second SAP may accumulate in the valleys presented by the substrate 2. The support roll 106 then carries the second substrate 6 past the rotating printing roll 108 which transfers the absorbent particulate polymer material from the first hopper 107 to the second substrate 6 in the grid pattern which is as illustrated in FIGS. 5 and 6 of 2008/0312617A1. A vacuum (not shown) in the printing roll 108 may hold the second superabsorbent particulate polymer material in the reservoirs until time to deliver the absorbent particulate polymer material to the second substrate 6. The vacuum may then be released or air flow through the air passages may be reversed to eject the absorbent particulate polymer material from the reservoirs and onto the second substrate 6. The absorbent particulate polymer material may accumulate in the valleys presented by the substrate 6. The support roll 106 then carries the printed second substrate 6 past the thermoplastic adhesive material applicator 110 which applies the fibrous layer of thermoplastic adhesive material 4 to cover the layer 3 of second SAP on the second substrate 6. This applicator may spray the thermoplastic adhesive material in a slightly narrower pattern as the deposition area 8 but as this spray of fibers is vacuumed into the second absorbent layer by the receiving support roll 106, which has the same pattern as the deposited SAP, it ends up covering most/all the surface of the printed SAP. The process may be conducted an intermittent thermoplastic adhesive material application, so the fibrous layer can be slightly longer than the deposition area of the layer of second SAP, but not as long as the full core.

Hence, the arrangement of reservoirs in the printing roll 108 and the uneven surface of the vented support grid of the support rolls 106 determine the distribution of absorbent particulate polymeric material throughout the second absorbent layer (land areas 9) and likewise determines the pattern of junction areas 10.

Meanwhile, the forming drum 124 draws the first substrate 2 past the second auxiliary adhesive applicator 114 which applies an auxiliary adhesive 116 to the first substrate 2 in a desired pattern. The forming drum 124 then carries the first substrate 2 in the mixing chamber 118 where the mixed layer 7 is deposited on the first substrate 2. The first and second absorbent layers then pass through the nip 136 between the support rolls 106 and 124 for compressing and combining the first absorbent layer and second absorbent layer together. A sealing unit and cutting unit (not represented) may be used to form the individual absorbent cores.

The individual absorbent cores 28 can then be integrated in an absorbent article using conventional converting techniques, typically this will be done on the same converting line used to make the core, so that there is no intermediate storage of the absorbent cores.

Within an absorbent article, the first absorbent layer of the absorbent core is placed closer to, i.e. is oriented towards the topsheet and facing upwards when in use, as represented in FIGS. 1 and 2.

Experimental Settings

Unless otherwise mentioned, the values indicated herein are measured according to the methods indicated herein below.

Centrifuge Retention Capacity (CRC)

The CRC measures the liquid absorbed by the superabsorbent polymer particles for free swelling in excess liquid. The CRC is measured according to EDANA method WSP 241.2-05.

Urine Permeability Measurement (UPM)

Urine Permeability Measurement System

This method determines the permeability of a swollen hydrogel (superabsorbent polymer) layer 1318. The equipment used for this method is described below and is represented in FIG. 20-23. This method is closely related to the SFC (Salt Flow Conductivity) test method of the prior art.

Figure 20:
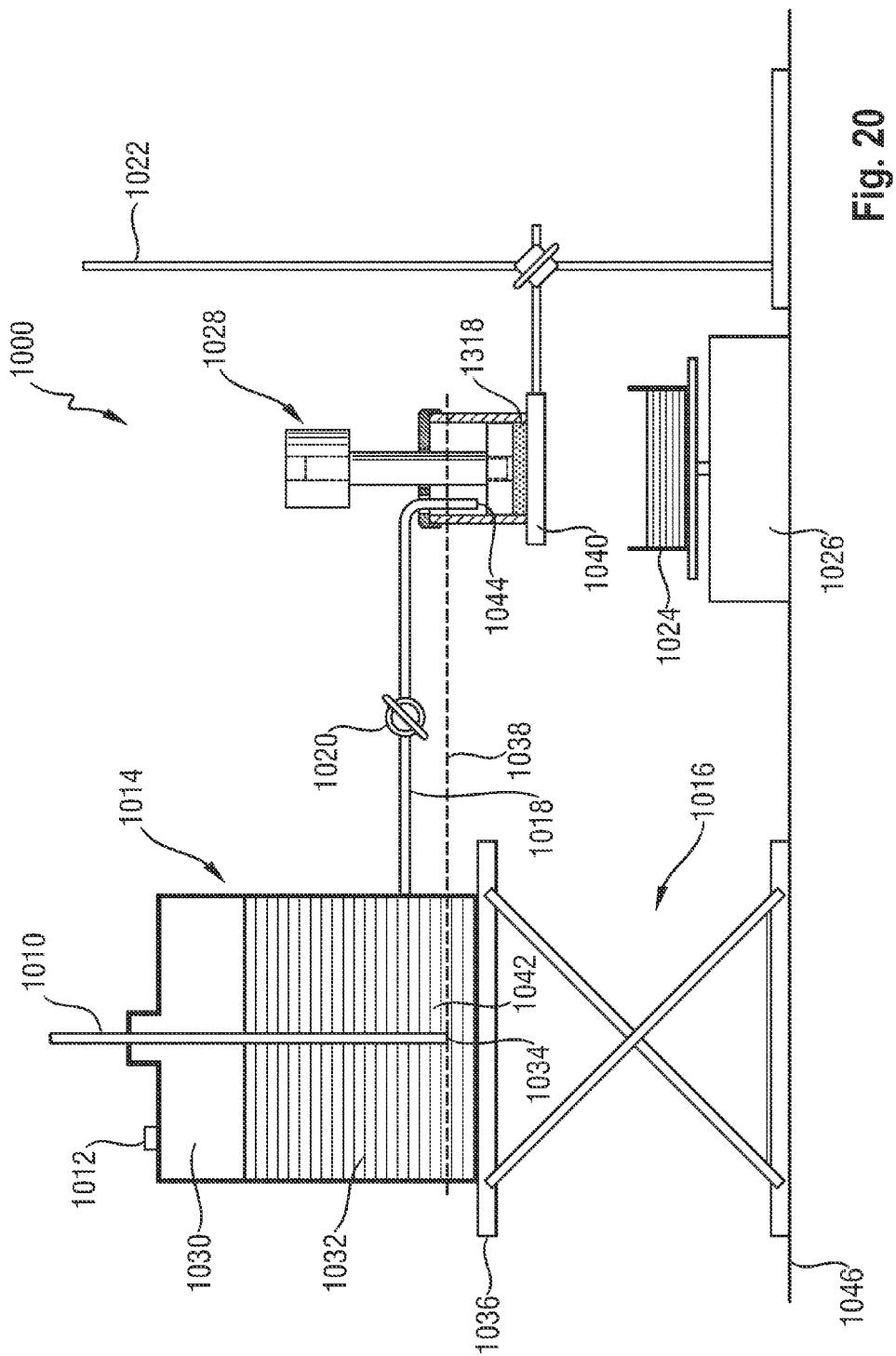
FIG. 20 is a partial cross-sectional side view of a suitable permeability measurement system for conducting the Urine Permeability Measurement Test.

FIG. 20 shows permeability measurement system 1000 set-up with the constant hydrostatic head reservoir 1014, open-ended tube for air admittance 1010, stoppered vent for refilling 1012, laboratory jack 1016, delivery tube 1018, stopcock 1020, ring stand support 1022, receiving vessel 1024, balance 1026 and piston/cylinder assembly 1028.

Figure 21:
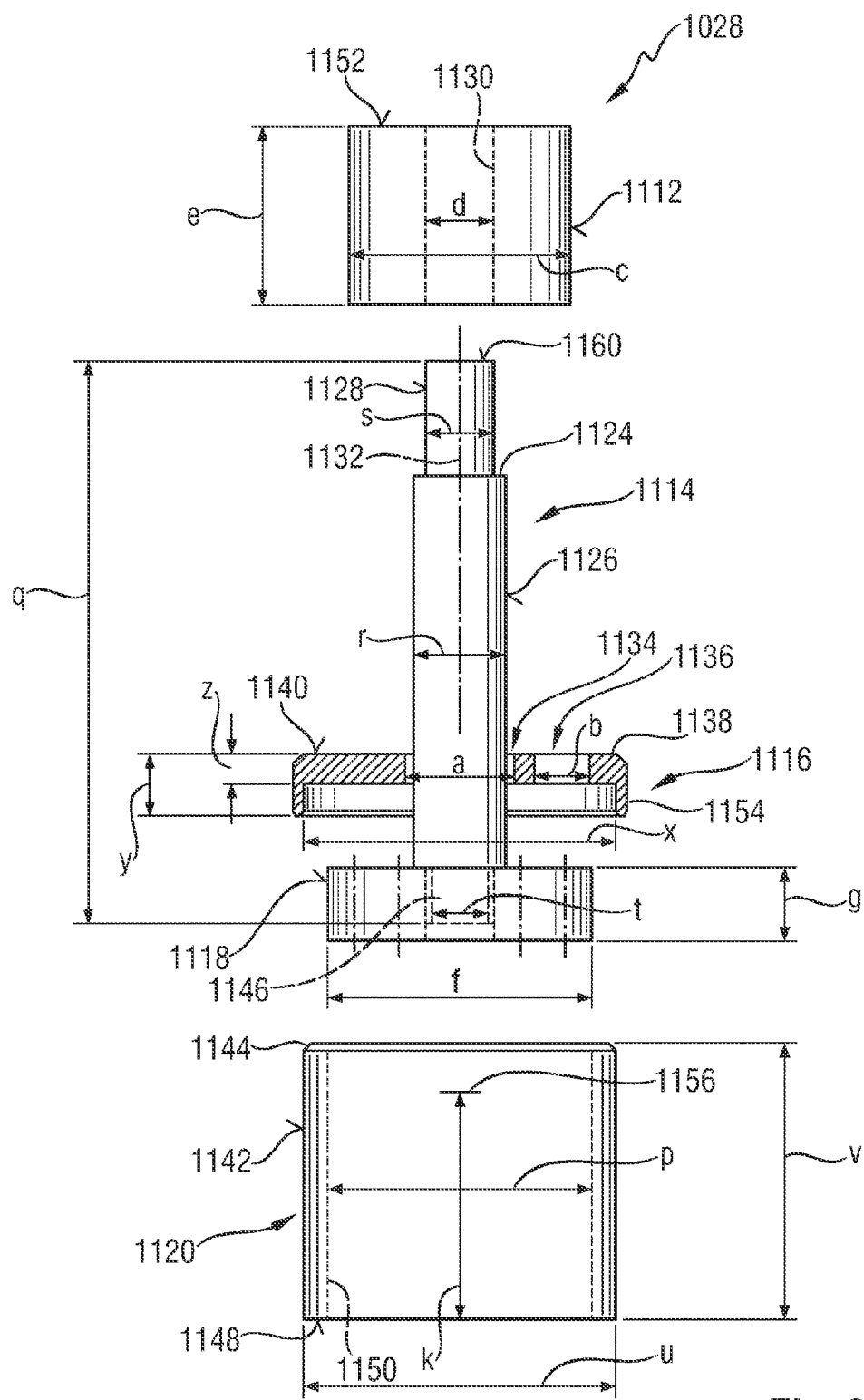
FIG. 21 is a cross-sectional side view of a piston/cylinder assembly for use in conducting the Urine Permeability Measurement Test.
Figure 22:
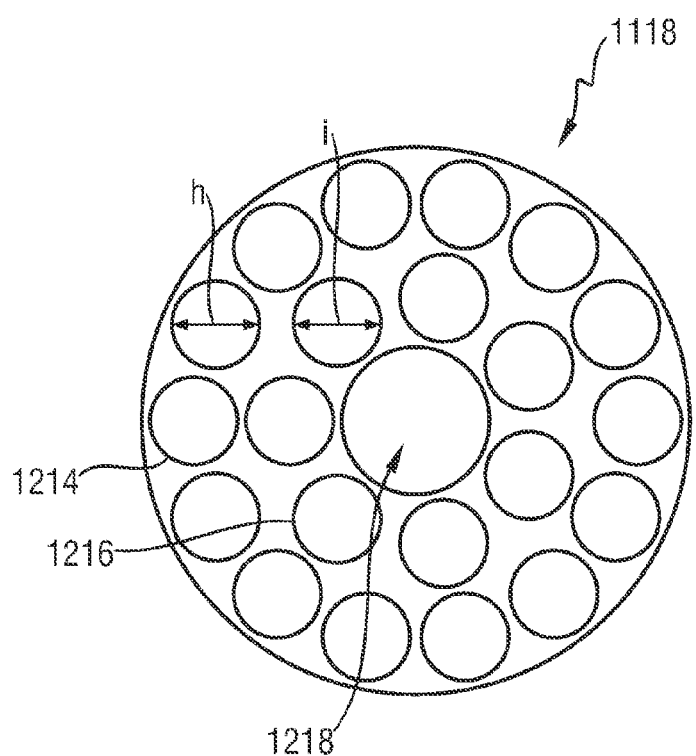
FIG. 22 is a top view of a piston head suitable for use in the piston/cylinder assembly shown in FIG. 21.
Figure 23:
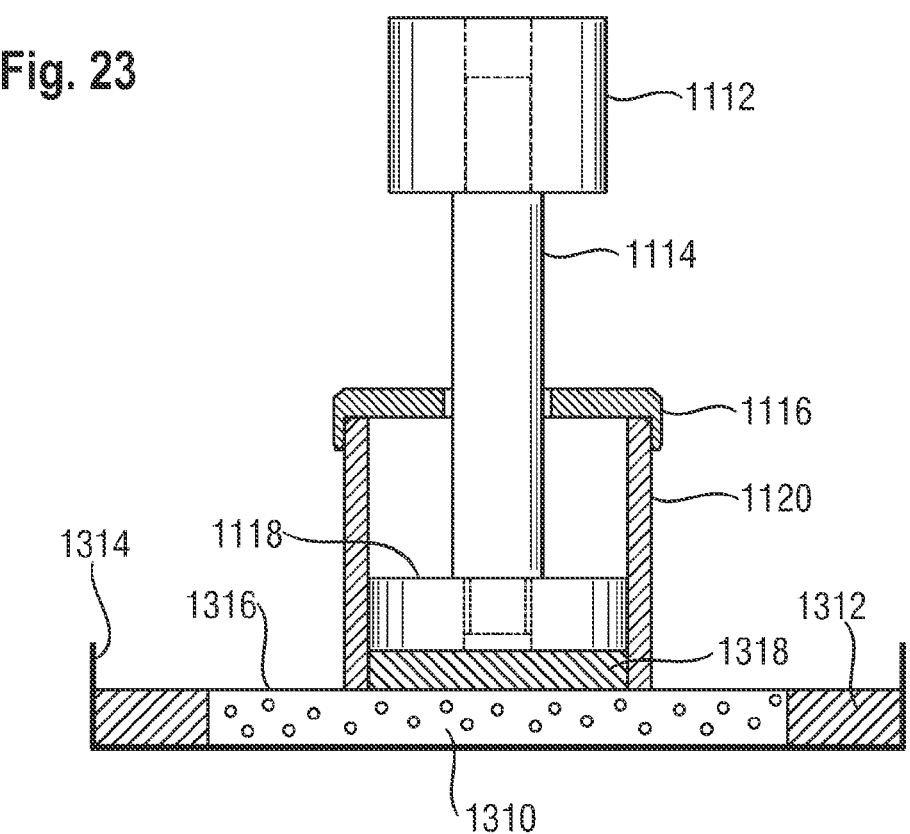
FIG. 23 is a cross-sectional side view of the piston/cylinder assembly of FIG. 22 placed on fritted disc for the swelling phase.

FIG. 21 shows the piston/cylinder assembly 1028 comprising a metal weight 1112, piston shaft 1114, piston head 1118, lid 1116, and cylinder 1120. The cylinder 1120 is made of transparent polycarbonate (e.g., Lexan®) and has an inner diameter p of 6.00 cm (area=28.27 $cm^2$) with inner cylinder walls 1150 which are smooth. The bottom 1148 of the cylinder 1120 is faced with a US. Standard 400 mesh stainless-steel screen cloth (not shown) that is bi-axially stretched to tautness prior to attachment to the bottom 1148 of the cylinder 1120. The piston shaft 1114 is made of transparent polycarbonate (e.g., Lexan®) and has an overall length q of approximately 127 mm. A middle portion 1126 of the piston shaft 1114 has a diameter r of 21.15 mm. An upper portion 1128 of the piston shaft 1114 has a diameter s of 15.8 mm, forming a shoulder 1124. A lower portion 1146 of the piston shaft 1114 has a diameter t of approximately ⅝ inch and is threaded to screw firmly into the center hole 1218 (see FIG. 17) of the piston head 1118. The piston head 1118 is perforated, made of transparent polycarbonate (e.g., Lexan®), and is also screened with a stretched US. Standard 400 mesh stainless-steel screen cloth (not shown). The weight 1112 is stainless steel, has a center bore 1130, slides onto the upper portion 1128 of piston shaft 1114 and rests on the shoulder 1124. The combined weight of the piston head 1118, piston shaft 1114 and weight 1112 is 596 g (±6 g), which corresponds to 0.30 psi over the area of the cylinder 1120. The combined weight may be adjusted by drilling a blind hole down a central axis 1132 of the piston shaft 1114 to remove material and/or provide a cavity to add weight. The cylinder lid 1116 has a first lid opening 1134 in its center for vertically aligning the piston shaft 1114 and a second lid opening 1136 near the edge 1138 for introducing fluid from the constant hydrostatic head reservoir 1014 into the cylinder 1120.

A first linear index mark (not shown) is scribed radially along the upper surface 1152 of the weight 1112, the first linear index mark being transverse to the central axis 1132 of the piston shaft 1114. A corresponding second linear index mark (not shown) is scribed radially along the top surface 1160 of the piston shaft 1114, the second linear index mark being transverse to the central axis 1132 of the piston shaft 1114. A corresponding third linear index mark (not shown) is scribed along the middle portion 1126 of the piston shaft 1114, the third linear index mark being parallel with the central axis 1132 of the piston shaft 1114. A corresponding fourth linear index mark (not shown) is scribed radially along the upper surface 1140 of the cylinder lid 1116, the fourth linear index mark being transverse to the central axis 1132 of the piston shaft 1114. Further, a corresponding fifth linear index mark (not shown) is scribed along a lip 1154 of the cylinder lid 1116, the fifth linear index mark being parallel with the central axis 1132 of the piston shaft 1114.

A corresponding sixth linear index mark (not shown) is scribed along the outer cylinder wall 1142, the sixth linear index mark being parallel with the central axis 1132 of the piston shaft 1114. Alignment of the first, second, third, fourth, fifth, and sixth linear index marks allows for the weight 1112, piston shaft 1114, cylinder lid 1116, and cylinder 1120 to be re-positioned with the same orientation relative to one another for each measurement.

The cylinder 1120 specification details are:
Outer diameter u of the Cylinder 1120: 70.35 mm
Inner diameter p of the Cylinder 1120: 60.0 mm
Height v of the Cylinder 1120: 60.5 mm
The cylinder lid 1116 specification details are:
Outer diameter w of cylinder lid 1116: 76.05 mm
Inner diameter x of cylinder lid 1116: 70.5 mm
Thickness y of cylinder lid 1116 including lip 1154: 12.7 mm
Thickness z of cylinder lid 1116 without lip 1154: 6.35 mm
Diameter a of first lid opening 1134: 22.25 mm
Diameter b of second lid opening 1136: 12.7 mm
Distance between centers of first and second lid openings 1134 and 1136: 23.5 mm
The weight 1112 specification details are:
Outer diameter c: 50.0 mm
Diameter d of center bore 1130: 16.0 mm
Height e: 39.0 mm
The piston head 1118 specification details are
Diameter f: 59.7 mm
Height g: 16.5 mm
Outer holes 1214 (14 total) with a 9.65 mm diameter h, outer holes 1214 equally spaced with centers being 47.8 mm from the center of center hole 1218
Inner holes 1216 (7 total) with a 9.65 mm diameter i, inner holes 1216 equally spaced with centers being 26.7 mm from the center of center hole 1218
Center hole 1218 has a diameter j of ⅝ inches and is threaded to accept a lower portion 1146 of piston shaft 1114.

Prior to use, the stainless steel screens (not shown) of the piston head 1118 and cylinder 1120 should be inspected for clogging, holes or over-stretching and replaced when necessary. A urine permeability measurement apparatus with damaged screen can deliver erroneous UPM results, and must not be used until the screen has been replaced.

A 5.00 cm mark 1156 is scribed on the cylinder 1120 at a height k of 5.00 cm (±0.05 cm) above the screen (not shown) attached to the bottom 1148 of the cylinder 1120. This marks the fluid level to be maintained during the analysis. Maintenance of correct and constant fluid level (hydrostatic pressure) is critical for measurement accuracy.

A constant hydrostatic head reservoir 1014 is used to deliver salt solution 1032 to the cylinder 1120 and to maintain the level of salt solution 1032 at a height k of 5.00 cm above the screen (not shown) attached to the bottom 1148 of the cylinder 1120. The bottom 1034 of the air-intake tube 1010 is positioned so as to maintain the salt solution 1032 level in the cylinder 1120 at the required 5.00 cm height k during the measurement, i.e., bottom 1034 of the air tube 1010 is in approximately same plane 1038 as the 5.00 cm mark 1156 on the cylinder 1120 as it sits on the support screen (not shown) on the ring stand 1040 above the receiving vessel 1024. Proper height alignment of the air-intake tube 1010 and the 5.00 cm mark 1156 on the cylinder 1120 is critical to the analysis. A suitable reservoir 1014 consists of a jar 1030 containing: a horizontally oriented L-shaped delivery tube 1018 for fluid delivery, a vertically oriented open-ended tube 1010 for admitting air at a fixed height within the constant hydrostatic head reservoir 1014, and a stoppered vent 1012 for re-filling the constant hydrostatic head reservoir 1014. Tube 1010 has an internal diameter of 12.5 mm±0.5 mm. The delivery tube 1018, positioned near the bottom 1042 of the constant hydrostatic head reservoir 1014, contains a stopcock 1020 for starting/stopping the delivery of salt solution 1032. The outlet 1044 of the delivery tube 1018 is dimensioned to be inserted through the second lid opening 1136 in the cylinder lid 1116, with its end positioned below the surface of the salt solution 1032 in the cylinder 1120 (after the 5.00 cm height of the salt solution 1032 is attained in the cylinder 1120). The air-intake tube 1010 is held in place with an o-ring collar (not shown). The constant hydrostatic head reservoir 1014 can be positioned on a laboratory jack 1016 in order to adjust its height relative to that of the cylinder 1120. The components of the constant hydrostatic head reservoir 1014 are sized so as to rapidly fill the cylinder 1120 to the required height (i.e., hydrostatic head) and maintain this height for the duration of the measurement. The constant hydrostatic head reservoir 1014 must be capable of delivering salt solution 1032 at a flow rate of at least 3 g/sec for at least 10 minutes.

The piston/cylinder assembly 1028 is positioned on a 16 mesh rigid stainless steel support screen (not shown) (or equivalent) which is supported on a ring stand 1040 or suitable alternative rigid stand. This support screen (not shown) is sufficiently permeable so as to not impede salt solution 1032 flow and rigid enough to support the stainless steel mesh cloth (not shown) preventing stretching. The support screen (not shown) should be flat and level to avoid tilting the piston/cylinder assembly 1028 during the test. The salt solution 1032 passing through the support screen (not shown) is collected in a receiving vessel 1024, positioned below (but not supporting) the support screen (not shown). The receiving vessel 1024 is positioned on the balance 1026 which is accurate to at least 0.01 g. The digital output of the balance 1026 is connected to a computerized data acquisition system (not shown).

Preparation of Reagents (not Illustrated)

Jayco Synthetic Urine (JSU) 1312 is used for a swelling phase (see UPM Procedure below) and 0.118 M Sodium Chloride (NaCl) Solution is used for a flow phase (see UPM Procedure below). The following preparations are referred to a standard 1 liter volume. For preparation of volumes other than 1 liter, all quantities are scaled accordingly.

JSU: A 1 L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of salts to make 1 liter of Jayco Synthetic Urine:
Potassium Chloride (KCl) 2.00 g
Sodium Sulfate ($Na_2SO_4$) 2.00 g
Ammonium dihydrogen phosphate ($NH_4H_2PO_4$) 0.85 g
Ammonium phosphate, dibasic (($NH_4$)$_2HPO_4$) 0.15 g
Calcium Chloride ($CaCl_2$) 0.19 g—[or hydrated calcium chloride ($CaCl_2.2H_2O$) 0.25 g]
Magnesium chloride ($MgCl_2$) 0.23 g—[or hydrated magnesium chloride ($MgCl_2.6H_2O$) 0.50 g]

To make the preparation faster, each salt is completely dissolved before adding the next one. Jayco synthetic urine may be stored in a clean glass container for 2 weeks. The solution should not be used if it becomes cloudy. Shelf life in a clean plastic container is 10 days.

0.118 M Sodium Chloride (NaCl) Solution: 0.118 M Sodium Chloride is used as salt solution 1032. Using a weighing paper or beaker 6.90 g (±0.01 g) of sodium chloride is weighed and quantitatively transferred into a 1 L volumetric flask; and the flask is filled to volume with distilled water. A stir bar is added and the solution is mixed on a stirring plate until all the solids are dissolved.

Test Preparation

Using a solid reference cylinder weight (not shown) (40 mm diameter; 140 mm height), a caliper gauge (not shown) (e.g., Mitotoyo Digimatic Height Gage) is set to read zero. This operation is conveniently performed on a smooth and level bench top 1046. The piston/cylinder assembly 1028 without superabsorbent polymer particles is positioned under the caliper gauge (not shown) and a reading, $L_1$, is recorded to the nearest 0.01 mm.

The constant hydrostatic head reservoir 1014 is filled with salt solution 1032. The bottom 1034 of the air-intake tube 1010 is positioned so as to maintain the top part (not shown) of the liquid meniscus (not shown) in the cylinder 1120 at the 5.00 cm mark 1156 during the measurement. Proper height alignment of the air-intake tube 1010 at the 5.00 cm mark 1156 on the cylinder 1120 is critical to the analysis.

The receiving vessel 1024 is placed on the balance 1026 and the digital output of the balance 1026 is connected to a computerized data acquisition system (not shown). The ring stand 1040 with a 16 mesh rigid stainless steel support screen (not shown) is positioned above the receiving vessel 1024. The 16 mesh screen (not shown) should be sufficiently rigid to support the piston/cylinder assembly 1028 during the measurement. The support screen (not shown) must be flat and level.

UPM Procedure 1.5 g (±0.05 g) of superabsorbent polymer particles is weighed onto a suitable weighing paper or weighing aid using an analytical balance. The moisture content of the superabsorbent polymer particles is measured according to the Edana Moisture Content Test Method 430.1-99 ("Superabsorbent materials—Polyacrylate superabsorbent powders—Moisture Content—weight loss upon heating" (February 99)). If the moisture content of the superabsorbent polymer particles is greater than 5%, then the superabsorbent polymer particles weight should be corrected for moisture (i.e., in that particular case the added superabsorbent polymer particles should be 1.5 g on a dry-weight basis).

The empty cylinder 1120 is placed on a level benchtop 1046 and the superabsorbent polymer particles are quantitatively transferred into the cylinder 1120. The superabsorbent polymer particles are evenly dispersed on the screen (not shown) attached to the bottom 1148 of the cylinder 1120 by gently shaking, rotating, and/or tapping the cylinder 1120. It is important to have an even distribution of particles on the screen (not shown) attached to the bottom 1148 of the cylinder 1120 to obtain the highest precision result. After the superabsorbent polymer particles have been evenly distributed on the screen (not shown) attached to the bottom 1148 of the cylinder 1120 particles must not adhere to the inner cylinder walls 1150. The piston shaft 1114 is inserted through the first lid opening 1134, with the lip 1154 of the lid 1116 facing towards the piston head 1118. The piston head 1118 is carefully inserted into the cylinder 1120 to a depth of a few centimeters. The lid 1116 is then placed onto the upper rim 1144 of the cylinder 1120 while taking care to keep the piston head 1118 away from the superabsorbent polymer particles. The lid 1116 and piston shaft 1126 are then carefully rotated so as to align the third, fourth, fifth, and sixth linear index marks are then aligned. The piston head 1118 (via the piston shaft 1114) is then gently lowered to rest on the dry superabsorbent polymer particles. The weight 1112 is positioned on the upper portion 1128 of the piston shaft 1114 so that it rests on the shoulder 1124 such that the first and second linear index marks are aligned. Proper seating of the lid 1116 prevents binding and assures an even distribution of the weight on the hydrogel layer 1318.

Swelling Phase: An 8 cm diameter fritted disc (7 mm thick; e.g. Chemglass Inc. #CG 201-51, coarse porosity) 1310 is saturated by adding excess JSU 1312 to the fritted disc 1310 until the fritted disc 1310 is saturated. The saturated fritted disc 1310 is placed in a wide flat-bottomed Petri dish 1314 and JSU 1312 is added until it reaches the top surface 1316 of the fritted disc 1310. The JSU height must not exceed the height of the fitted disc 1310.

The screen (not shown) attached to the bottom 1148 of the cylinder 1120 is easily stretched. To prevent stretching, a sideways pressure is applied on the piston shaft 1114, just above the lid 1116, with the index finger while grasping the cylinder 1120 of the piston/cylinder assembly 1028. This "locks" the piston shaft 1114 in place against the lid 1116 so that the piston/cylinder assembly 1028 can be lifted without undue force being exerted on the screen (not shown).

The entire piston/cylinder assembly 1028 is lifted in this fashion and placed on the fritted disc 1310 in the Petri dish 1314. JSU 1312 from the Petri dish 1314 passes through the fritted disc 1310 and is absorbed by the superabsorbent polymer particles (not shown) to form a hydrogel layer 1318. The JSU 1312 available in the Petri dish 1314 should be enough for all the swelling phase. If needed, more JSU 1312 may be added to the Petri dish 1314 during the hydration period to keep the JSU 1312 level at the top surface 1316 of the fitted disc 1310. After a period of 60 minutes, the piston/cylinder assembly 1028 is removed from the fritted disc 1310, taking care to lock the piston shaft 1114 against the lid 1116 as described above and ensure the hydrogel layer 1318 does not lose JSU 1312 or take in air during this procedure. The piston/cylinder assembly 1028 is placed under the caliper gauge (not shown) and a reading, $L_2$, is recorded to the nearest 0.01 mm. If the reading changes with time, only the initial value is recorded. The thickness of the hydrogel layer 1318, $L_0$ is determined from $L_2-L_1$ to the nearest 0.1 mm.

The piston/cylinder assembly 1028 is transferred to the support screen (not shown) attached to the ring support stand 1040 taking care to lock the piston shaft 1114 in place against the lid 1116. The constant hydrostatic head reservoir 1014 is positioned such that the delivery tube 1018 is placed through the second lid opening 1136. The measurement is initiated in the following sequence:

a) The stopcock 1020 of the constant hydrostatic head reservoir 1014 is opened to permit the salt solution 1032 to reach the 5.00 cm mark 1156 on the cylinder 1120. This salt solution 1032 level should be obtained within 10 seconds of opening the stopcock 1020.

b) Once 5.00 cm of salt solution 1032 is attained, the data collection program is initiated.

With the aid of a computer (not shown) attached to the balance 1026, the quantity of salt solution 1032 passing through the hydrogel layer 1318 is recorded at intervals of 20 seconds for a time period of 10 minutes. At the end of 10 minutes, the stopcock 1020 on the constant hydrostatic head reservoir 1014 is closed.

The data from 60 seconds to the end of the experiment are used in the UPM calculation. The data collected prior to 60 seconds are not included in the calculation. The flow rate F, (in g/s) is the slope of a linear least-squares fit to a graph of the weight of salt solution 1032 collected (in grams) as a function of time (in seconds) from 60 seconds to 600 seconds.

The Urine Permeability Measurement (Q) of the hydrogel layer 1318 is calculated using the following equation:

$$Q=[F_g \times L_0]/[\rho \times A \times \Delta P],$$

where $F_g$ is the flow rate in g/sec determined from regression analysis of the flow rate results, $L_0$ is the initial thickness of the hydrogel layer 1318 in cm, $\rho$ is the density of the salt solution 1032 in g/cm$^3$. A (from the equation above) is the area of the hydrogel layer 1318 in cm$^2$, $\Delta P$ is the hydrostatic pressure in dyne/cm$^2$, and the Urine Permeability Measurement, Q, is in units of cm$^3$ sec/g. The average of three determinations should be reported.

Wet Channel Integrity Test

This test is designed to check the integrity of a channel following wet saturation. The test can be performed directly on an absorbent core. If an absorbent article is provided and the core is not available separately, the test can be performed on the absorbent article after removing the topsheet and any other intermediate layers for example acquisition layers, surge layers etc.

1. The length (in millimeters) of the channel is measured in the dry state (if the channel is not straight, the curvilinear length through the middle of the channel is measured).
2. The absorbent core is then immersed in 5 liters of synthetic urine "Saline", with a concentration of 9.00 g NaCl per 1000 ml solution prepared by dissolving the appropriate amount of sodium chloride in distilled water. The temperature of the solution must be 20+/−5° C.
3. After 1 minute in the saline, the absorbent core is removed and held vertically by one end for 5 seconds to drain, then extended flat on a horizontal surface with the garment-facing side down, if this side is recognizable. If the absorbent core comprises stretch elements, the absorbent core is pulled taut in both X and Y dimensions so that no contraction is observed. The extremes/edges of the absorbent core are fixed to the horizontal surface, so that no contraction can happen.
4. The absorbent core is covered with a suitably weighted rigid plate, with dimensions as follows: length equal to the extended length of the absorbent core, and width equal to the maximum absorbent core width in the cross direction.
5. A pressure of 18.0 kPa is applied for 30 seconds over the area of the rigid plate above mentioned. Pressure is calculated on the basis of overall area encompassed by the rigid plate. Pressure is achieved by placing additional weights in the geometric center of the rigid plate, such that the combined weight of the rigid plate and the additional weights result in a pressure of 18.0 kPa over the total area of the rigid plate.
6. After 30 seconds, the additional weights and the rigid plate are removed.
7. Immediately afterwards, the cumulative length of the portions of the channel which remained intact by visual determination is measured (in millimeters; if the channel is not straight, the curvilinear length through the middle of the channel is measured). If no portions of the channel remained intact then the channel is not permanent.
8. The percentage of integrity of the permanent channel is calculated by dividing the cumulative length of the portions of the channel which remained intact by the length of the channel in the dry state, and then multiplying the quotient by 100.

AGM Immobilization Test (Free AGM)

This method determines the free absorbent particulate material amount, in dry conditions, in an absorbent article or core using a vibrating unit. This free AGM can build up agglomerates and beyond a certain amount of free AGM it leads to increased consumer complaints.

Principle: An absorbent article or core is cut in half along its transversal axis and each half is clamped vertically in a planar configuration with the cut end facing downwards. A wedge of specified dimensions is inserted vertically into the primary AGM-containing layer of the absorbent article or the core from the cut end along the longitudinal axis. The absorbent article or core, supporting structure, and wedge are vibrated as a single structure horizontally in a linear direction orthogonal to the plane of the article or core for a specified time. Thus the diaper is not vibrated relative to the wedge. The process is repeated for the other half of the absorbent article or core and any AGM particles dislodged from the article or core during the vibration periods are collected and weighed to determine the fraction of AGM dislodged.

Figure 24:
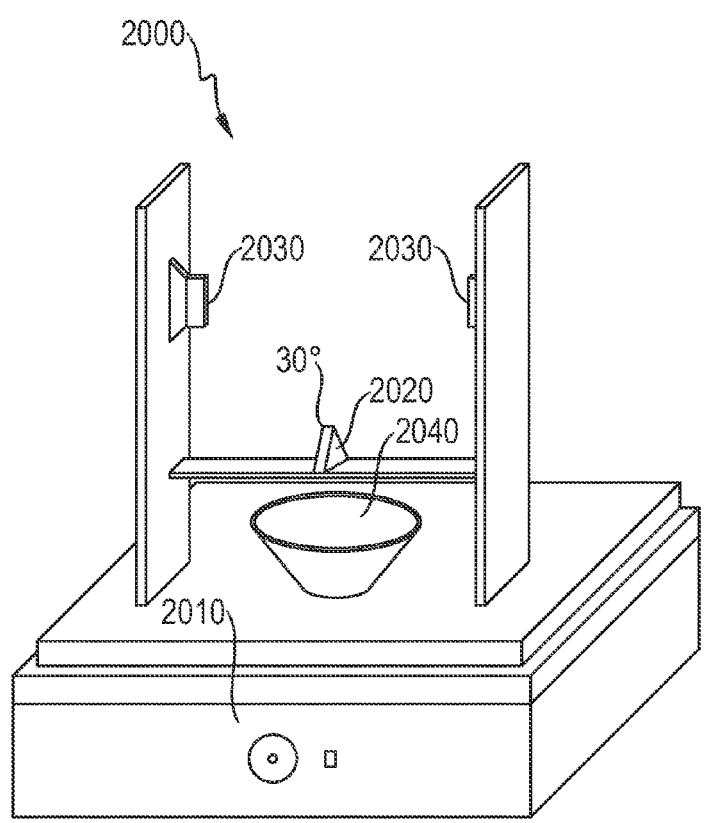
FIG. 24 shows a simplified drawing of a scaffolding and vibration unit which can be used to conduct the AGM Immobilization Test (Free AGM).

Apparatus: Scaffolding and Vibration Unit,

FIG. 24 shows a simplified drawing of a scaffolding and vibration unit 2000 which can be used for size 4 diapers. The vibrating table 2010 has a lateral oscillation with the following properties:

Waveform: Sinusoidal
Amplitude: 2 mm
Frequency: 47 Hz (+/−1 Hz)
Vibrating time: 10 s (+/−0.5 s)

The wedge 2020 is introduced 7.5 cm into the cut opening of the core which is held by the clamps 2030 as per the description of the method below. The wedge is 7.5 mm long, 40 mm wide in the base, and with a caliper of 10 mm.

Sample Preparation and Test Method

1) A suitable empty bowl 2040 is tared on a balance to within ±0.01 g
2) The absorbent core is extended topsheet side up and placed flat onto a table. Any ears and/or elastics are removed without compromising the integrity of the absorbent article.
3) The absorbent core is cut in half along the transverse axis. Any absorbent particulate material dislodged from the product during cutting is collected in the bowl D and is included in the total mass of dislodged absorbent material.
4) One half of the absorbent core being tested is held cut edge up and an opening no more than 5 mm in width or depth is made in the center of the cut edge to separate the layers in the article in this region. This opening/section of the absorbent article is then carefully pulled over the wedge A of the apparatus so that the tip of the wedge protrudes 7.5 cm into the core from the cut end along the longitudinal axis. Any absorbent particulate material dislodged during this step is captured in the bowl D.
5) The lateral edges of the absorbent core are clamped in the clamps B such that the core is held substantially in a vertical planar configuration and the absorbent core is not within the clamps.

6) The scaffolding supporting the core is vibrated horizontally in a linear direction orthogonal to the plane of the core for 10.0 seconds while the wedge remains stationary. The vibration has a sinusoidal waveform with amplitude of 2.00 mm, and a frequency of 47.0 Hz. Any absorbent material dislodged from the product is collected in bowl D.

7) Steps 4 to 6 are repeated with the other half of the absorbent article.

8) The total weight of absorbent material dislodged from the absorbent core in steps 1 to 7 is added and reported.

EXAMPLES

Invention Example

The first substrate (herein referred to as "core cover") was a hydrophilic coated PP (polypropylene) nonwoven material, with Spunbonded, Meltblown, Meltblown, and Spunbonded layers forming an SMMS structure. The basis weight of each M-layer was 1 gsm and the basis weight of each S-Layer 4 gsm, resulting in a material with an overall basis weight of 10 gsm. The material was coated with a surfactant to be hydrophilic. The core cover had a width of 175 mm and a length of 414 mm.

The second substrate (herein referred to as "dusting layer") used was a hydrophobic non coated PP nonwoven material, with Spunbonded, Meltblown, Meltblown, and Spunbonded layers forming an SMMS structure. The basis weight of each M-layer was 1 gsm and the basis weight of each S-Layer 4 gsm, resulting in a material with an overall basis weight of 10 gsm. The dusting layer had a width of 140 mm and a length of 414 mm. The same substrates were used in the comparative example.

The mixed SAP/airfelt (AF) layer was made with a first SAP sourced as AQUALIC CA (Type L520) and fluff pulp 757 GSM SuperSoft Plus made by International Paper/Georgetown fluff pulp mill. An homogenous mixture for a total of 4.5 g of SAP and 4.5 g of fluff pulp was used. The mixed layer was 414 mm long and had a width of 120 mm from the front edge until a distance of 63 mm from the front edge, the width then linearly reduces from 120 mm to 90 mm between 63 mm and 103 mm from the front edge, then stays at 90 mm between 103 mm and 202 mm from the front edge, the width then increases linearly from 90 to 120 mm between 202 mm and 302 mm from the front edge, the width then stays at 120 mm between 302 mm and 414 mm from the front edge. The shape was symmetric vs. the core longitudinal axis.

The indicated AF and first SAP amounts were distributed along the longitudinal direction of the core as follows: 1.20 g of AF and 1.20 g of SAP from the front edge until a distance of 109.5 mm from the front edge, 1.20 g of AF and 1.20 g of SAP between 109.5 mm and 219 mm from the front edge, 1.20 g of AF and 1.20 g of SAP between 219 mm and 328.5 mm from the front edge, 0.9 g of AF and 0.9 g of SAP between 328.5 mm and 414 mm from the front edge.

The shaped mixed SAP/AF layer was attached to the nonwoven core cover with a high frequency sinusoidal fiber spray layer of auxiliary glue having a basis weight of 1.83 gsm, a width of 100 mm and a length 414 mm.

Glue HL1358LO available from HB Fuller was applied as an auxiliary adhesive onto the nonwoven dusting layer as 41 slots 1 mm wide a spaced by 1 mm such to cover a pattern 81 mm wide and 310 mm long centered versus the longitudinal axis of the core, such that the basis weight was 5 gsm. The second SAP layer was bonded to the auxiliary glue. The second SAP were sourced as AQUALIC CA (Type L520), having a CRC of 30 g/g and a UMP of 50 $10^{-7}$ cm$^3$ sec/g. A total of 8.6 g of second SAP was used.

The deposition area of the second SAP was 300 mm long and had a width of 120 mm from the front edge until a distance of 58 mm from the front edge, the width then linearly reduced from 120 mm to 90 mm between 58 mm and 98 mm from the front edge, the width then stayed at 90 mm between 98 mm and 197 mm from the front edge, the width then increased linearly from 90 to 120 mm between 197 mm and 297 mm from the front edge, the width then stayed 120 mm between 297 mm and 300 mm from the front edge. The shape was symmetric along the core longitudinal axis.

The second SAP amount was distributed along the longitudinal direction of the core as follows: 3.38 g of SAP from the front edge until a distance of 109.5 mm from the front edge, 4.03 g of SAP between 109.5 mm and 219 mm from the front edge, 1.18 g of SAP between 219 mm and 328.5 mm from the front edge, 0 g of SAP between 328.5 mm and 414 mm from the front edge. The SAP were applied in a transversal bar pattern with bars (land areas) being 10 mm wide and having a distance of about 2 mm between each bar (junction areas).

In total the invention example had 13.1 g of first and second SAP and 4.5 g of airfelt.

The microfiber glue NW1151 ex HB Fuller was applied onto the second SAP layer as a fibrous adhesive layer pattern having a width of 118 mm, a length of 310 mm and a basis weight of 10 gsm, being the pattern symmetric versus the longitudinal axis of the core.

The shaped second SAP layer was bonded to the mixed layer with a spray layer of construction glue available from HB Fuller, having a basis weight of 2 gsm, a width of 100 mm and a length 414 mm. The construction glue was applied uniformly onto the fibrous adhesive layer described above.

The core was sealed with 2 slots of adhesive applied onto the nonwoven core cover at a distance of 150 mm, each slot having a basis weight of 20 gsm, a width of 4 mm and a length 414 mm: as adhesive HL1358LO ex HB Fuller was used and the core cover was folded to a width of 130 mm such that the 2 adhesive slots have been attached to the nonwoven dusting layer in a C-wrap.

Comparative Example

The used core cover was a hydrophilic coated PP (polypropylene) nonwoven material, with Spunbonded, Meltblown, Meltblown, and Spunbonded layers forming an SMMS structure. The basis weights of the M-layers are 1 gsm and the S-Layers 3 gsm, resulting in a material with an overall basis weight of 8 gsm. The material was coated with PHP26 (Schill&Seilacher) with an add-on level between 0.5-0.8% (EDANA WSP 353.0 (08)) to be hydrophilic. The core cover has a width of 166 mm and a length of 414 mm.

The used dusting layer was a hydrophobic non coated PP nonwoven material, with Spunbonded, Meltblown, Meltblown, and Spunbonded layers forming an SMMS structure. The basis weight of each M-layers was 1 gsm and each S-Layer 3 gsm, resulting in a material with an overall basis weight of 8 gsm. The dusting layer had a width of 134 mm and a length of 414 mm.

The mixed SAP/airfelt layer was made with AQUALIC CA (Type L520) available from Nippon Shokubai, having a CRC of 30 g/g and a UMP of 50 $10^{-7}$ cm$^3$ sec/g and fluff pulp 757 GSM SuperSoft Plus made by International Paper/Georgetown fluff pulp mill. A blend of SAP and AF for a total of 12.7 g of SAP and 7.3 g AF was used, those amounts being comparable to the amounts used in the invention example.

The mixed layer was 414 mm long and had a width of 116 mm from the front edge until a distance of 63 mm from the front edge, it was then linearly reduced from 116 mm to 90 mm between 63 mm and 103 mm from the front edge, it was then 90 mm between 103 mm and 202 mm from the front edge, it then increased linearly from 90 to 116 mm between 202 mm and 302 mm from the front edge, it was 116 mm between 302 mm and 414 mm from the front edge. The shape must be intended symmetric vs. the core longitudinal axis.

The indicated AF and SAP amounts were distributed along the longitudinal axis of the core as follows: 2.26 g of AF and 3.94 g of SAP from the front edge, until a distance of 109.5 mm from the front edge, 1.68 g of AF and 4.29 g of SAP between 109.5 mm and 219 mm from the front edge, 1.75 g of AF and 3.18 g of SAP between 219 mm and 328.5 mm from the front edge, 1.61 g of AF and 1.29 g of SAP between 328.5 mm and 414 mm from the front edge.

The shaped mixed SAP/AF layer was bonded to the nonwoven core cover with a high frequency sinusoidal fiber spray layer of construction glue D3155b Zeropack available from HB Fuller, having a basis weight of 1.8 gsm, a width of 100 mm and a length 414 mm. The shaped mixed SAP/AF layer was bonded to the nonwoven dusting layer with a high frequency sinusoidal fiber spray layer of construction glue D3155b Zeropack available from HB Fuller, having a basis weight of 1 gsm, a width of 100 mm and a length 414 mm.

The core was sealed using a sandwich wrap with 2 slots of adhesive at a distance of 140 mm, each slot having a basis weight of 12 gsm, a width of 3 mm and a length 414 mm, with 2 slots of adhesive at a distance of 109 mm, each slot having a basis weight of 12 gsm, a width of 3 mm and a length 414 mm, and with 2 slots of adhesive at a distance of 98 mm: each slot having a basis weight of 12 gsm, a width of 7 mm and a length 414 mm as adhesive DM526 available from Henkel was used between the nonwoven core cover and the nonwoven dusting layer.

Prototype Diapers

Diaper prototypes have been produced using Pampers Baby Dry size 4 diapers commercially available in Germany in April 2012, replacing the commercial core in these diapers by the Cores according to the Examples above (the first absorbent layer placed towards the topsheet). Those diapers were compacted in a bag at an In Bag Stack Height, i.e. the total caliper of 10 bi-folded diapers, of 80 mm for 1 week, have then been taken out of the bag for 1 day The diaper prototypes were analyzed according to Rewet Test set out below. The AGM Immobilization Test (Free AGM) and Wet Immobilization test (WAIIT) were conducted directly on the Cores.

Rewet Test

In short, this method is used to compare the rewet at the surface of the diapers after it has been submitted to 4 saline solution gushes in a standardized way. The amount of rewet is measured by weighting the amount of fluid absorbed by collagen sheets applied under a given pressure on the topsheet of the diapers. Three diapers according to the invention were tested and four for the comparative example. The results showed parity between the invention examples and the comparative examples in terms of rewet performance (137 vs 132 mg of fluid, with a standard deviation of 22 and 27 mg respectively).

AGM Immobilization Test (Free AGM)

The test was conducted as indicated above and the results were as follows, considered to show an improvement of at least 90% statistical confidence vs. the Comparative Example.

|  | Invention Example | | Comparative Example | |
| --- | --- | --- | --- | --- |
|  | avg | stdev | avg | stdev |
| Free AGM [g] | 0.09 | 0.02 | 1.1 | 0.2 |

Wet Immobilization Test (WAIIT)

In short, this method determines the amount of non-immobilized absorbent particulate material amount in the cores in wet conditions. The absorbent core is wet to 73% capacity and is cut in its middle in the transversal direction and left to fall from a pre-determined height and loss of material is measured. Further information regarding the test can be found in US 2010/0051166A1. The results were as follows, considered to show an improvement at 90% statistical confidence vs. the Comparative Example.

|  | Invention Example | | Comparative Example | |
| --- | --- | --- | --- | --- |
|  | avg | stdev | avg | stdev |
| Dry weight [g] | 20.0 | 0.1 | 21.3 | 0.8 |
| Wet full pad [g] | 309.6 | 1.1 | 303.2 | 1.5 |
| AGM loss [g] | 211.7 | 6.0 | 283.3 | 2.5 |
| AGM loss [%] | 68 | 2 | 94 | 1 |
| Wet Immobilization [%] | 32 | 2 | 6 | 1 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a topsheet, a backsheet and an absorbent core disposed between the topsheet and the backsheet, wherein the absorbent core comprises:

a first absorbent layer comprising a first substrate and a mixed layer deposited on the first substrate, the mixed layer comprising a mixture of first superabsorbent polymer particles and cellulosic fibers; and a second absorbent layer comprising a second substrate, a layer of second superabsorbent polymer particles deposited on the second substrate, and a fibrous layer of thermoplastic adhesive material covering the layer of second superabsorbent polymer particles, wherein the layer of second superabsorbent polymer particles is substantially cellulose free;

wherein the first absorbent layer and the second absorbent layer are combined such that at least a portion of the fibrous layer of thermoplastic adhesive material of the second absorbent layer contacts at least a portion of the mixed layer of the first absorbent layer, and wherein the first absorbent layer is placed closer to the topsheet than the second absorbent layer, and wherein the core has a longitudinal axis, and wherein the second absorbent layer comprises one or more channels substantially extending in the longitudinal direction of the core, the channels being free of the second superabsorbent polymer particles and each channel being defined by continuous side wall portions; wherein in the channels the second substrate is bonded to the side wall portions; and wherein the first substrate is C-wrapped along longitudinal edges of the core to form C-flaps and the second substrate is disposed inwardly of these C-flaps.

2. The absorbent article according to claim 1, wherein the deposition area of the layer of second superabsorbent polymer particles comprises discrete land areas separated by junction areas substantially free of the second superabsorbent polymer particles.

3. The absorbent article according to claim 2, wherein the fibrous layer of thermoplastic adhesive material covers the land areas and the junction areas.

4. The absorbent article according to claim 2, wherein the core has a longitudinal axis, and wherein the basis weight of the second superabsorbent polymer particles in the land areas varies to form a profiled distribution of the second superabsorbent polymer particles in the direction of the longitudinal axis of the core.

5. The absorbent article according to claim 1, wherein a length of the one or more channels is at least 20% of a length of the core and a width of the one or more channels is at least 5 mm.

6. The absorbent article according to claim 1, wherein the first absorbent layer comprises one or more channels substantially extending in the longitudinal direction of the core.

7. The absorbent article according to claim 6, wherein the one or more channels of the first and second absorbent layers are at least partially overlapping and the first and second substrates are bonded to each other through the one or more channels.

8. The absorbent article according to claim 1, wherein the first substrate and the second substrate are made of nonwoven materials, and wherein the first substrate is more hydrophilic than the second substrate.

9. The absorbent article according to claim 1, comprising a first auxiliary adhesive disposed between the first substrate and the mixed layer.

10. The absorbent article according to claim 1, comprising a second auxiliary adhesive disposed between the second substrate and the layer of second superabsorbent polymer particles.

11. The absorbent article according to claim 1, wherein the first superabsorbent polymer particles and the second superabsorbent polymer particles are made of different materials.

12. The absorbent article according to claim 11, wherein the first superabsorbent polymer particles have a lower Urine Permeability Measurement than the second superabsorbent polymer particles.

13. The absorbent article according to claim 1, wherein the mixed layer comprises a homogeneous mix of first superabsorbent polymer particles and cellulosic fibers, and wherein the mixed layer comprises from 10% to 70% of the first superabsorbent polymer particles by total weight of the mixed layer.

14. The absorbent article according to claim 1, wherein the basis weight of the mixed layer is uniform across the area of deposition of the first absorbent layer.

15. The absorbent article according to claim 1, wherein at least one of the layer of second superabsorbent absorbent polymer particles and the mixed layer are deposited in a non-rectangular deposition pattern on their respective substrate.

16. The absorbent article according to claim 1, wherein the deposition area of the layer of the second superabsorbent polymer particles is smaller than the deposition area of the mixed layer.

17. The absorbent article according to claim 1, comprising an acquisition layer or acquisition system between the topsheet and the absorbent core.

18. The absorbent article according to claim 17, wherein the acquisition layer or system comprises at least one layer comprising cross-linked cellulose fibers.

* * * * *